(12) United States Patent
Ainsworth et al.

(10) Patent No.: US 7,938,836 B2
(45) Date of Patent: May 10, 2011

(54) DRIVER ASSEMBLY FOR SIMULTANEOUS AXIAL DELIVERY OF SPINAL IMPLANTS

(75) Inventors: Stephen D. Ainsworth, Wilmington, NC (US); Robert L. Assell, St. Paul, MN (US); Bradley J. Wessman, Wilmington, NC (US)

(73) Assignee: TranS1, Inc., Wilmington, NC (US)

( * ) Notice: Subject to any disclaimer, the term of this patent is extended or adjusted under 35 U.S.C. 154(b) by 1553 days.

(21) Appl. No.: 11/259,614

(22) Filed: Oct. 25, 2005

(65) Prior Publication Data

US 2006/0155297 A1    Jul. 13, 2006

Related U.S. Application Data

(63) Continuation-in-part of application No. 11/256,810, filed on Oct. 24, 2005, now Pat. No. 7,601,171, and a continuation-in-part of application No. 10/972,184, filed on Oct. 22, 2004, now Pat. No. 7,717,958, and a continuation-in-part of application No. 10/972,039, filed on Oct. 22, 2004, now Pat. No. 7,491,236, and a continuation-in-part of application No. 10/972,040, filed on Oct. 22, 2004, now Pat. No. 7,662,173, and a continuation-in-part of application No. 10/972,176, filed on Oct. 22, 2004, now Pat. No. 7,547,324, and a continuation-in-part of application No. 11/199,541, filed on Aug. 8, 2005, now abandoned.

(60) Provisional application No. 60/621,148, filed on Oct. 22, 2004, provisional application No. 60/621,730, filed on Oct. 25, 2004, provisional application No. 60/558,069, filed on Mar. 31, 2004, provisional application No. 60/513,899, filed on Oct. 23, 2003, provisional application No. 60/599,989, filed on Aug. 9, 2004.

(51) Int. Cl.
*A61B 17/58* (2006.01)

(52) U.S. Cl. .......................................................... 606/99

(58) Field of Classification Search .................. 606/104; 81/439, 442–449, 459, 461; 411/413, 384, 411/390
See application file for complete search history.

(56) References Cited

U.S. PATENT DOCUMENTS 640,661 A    1/1900   Johnstone ..................... 411/380
(Continued)

FOREIGN PATENT DOCUMENTS

WO    WO 9100713 A1    1/1991

*Primary Examiner* — Thomas C Barrett
*Assistant Examiner* — Nicholas Woodall
(74) *Attorney, Agent, or Firm* — The Eclipse Group LLP; Kevin E. Flynn

(57) ABSTRACT

Tools for use in the deployment of spinal implant assemblies such as spinal motion preservation assemblies adapted for use in a spinal motion segment are disclosed including the process for delivering and assembling the spinal motion preservation assemblies in the spinal motion segment via an axial channel created with a trans-sacral approach. The tools allow the deployment of a pair of spinal implant components that are not rigidly connected to one another to be driven into adjacent vertebral bodies. The tools further allow for distraction via either dissimilar thread pitch or by axially advancing a distraction tool based on a threaded engagement with a proximal component in a proximal vertebral body to impose an distraction between that vertebral body and an adjacent distal vertebral body. The tools also allow for the provision of flowable biomaterials such as prosthetic nucleus material. Delivery of flowable biomaterials can be performed while the vertebrae are being held apart by a distraction tool.

35 Claims, 24 Drawing Sheets

U.S. PATENT DOCUMENTS

| | | | |
|---|---|---|---|
| 1,007,107 A | 10/1911 | Hulsmann | |
| 1,029,104 A | 6/1912 | Clark | 411/379 |
| 1,079,224 A | 11/1913 | Dodds | 411/380 |
| 1,086,144 A | 2/1914 | Dodds | 411/379 |
| 1,111,691 A | 9/1914 | Flannery | 411/380 |
| 2,243,717 A * | 5/1941 | Moreira | 606/65 |
| 2,329,398 A | 9/1943 | Duffy | |
| 2,550,866 A * | 5/1951 | Rosan | 81/53.2 |
| 2,586,556 A | 2/1952 | Mullikin | 411/339 |
| 3,272,541 A | 9/1966 | Latzen | 403/138 |
| 3,367,326 A | 2/1968 | Frazier | 606/86 A |
| 3,837,347 A | 9/1974 | Tower | |
| 4,175,555 A | 11/1979 | Herbert | 606/304 |
| 4,276,874 A | 7/1981 | Wolvek et al. | |
| 4,297,047 A | 10/1981 | Farrant | 403/138 |
| 4,309,777 A | 1/1982 | Patil | |
| 4,636,217 A | 1/1987 | Ogilvie et al. | |
| 4,854,797 A | 8/1989 | Gourd | |
| 4,858,601 A * | 8/1989 | Glisson | 606/916 |
| 4,875,794 A | 10/1989 | Kern, Jr. | 403/132 |
| 4,878,915 A | 11/1989 | Brantigan | |
| 4,932,925 A | 6/1990 | Roinestad et al. | 474/206 |
| 4,932,975 A | 6/1990 | Main et al. | 623/17.12 |
| 4,959,064 A | 9/1990 | Engelhardt | 606/65 |
| 5,002,576 A | 3/1991 | Fuhrmann et al. | |
| 5,059,193 A | 10/1991 | Kuslich | |
| 5,061,137 A | 10/1991 | Gourd | |
| 5,078,718 A * | 1/1992 | Moll et al. | 606/86 R |
| 5,102,276 A | 4/1992 | Gourd | |
| 5,108,430 A | 4/1992 | Ravo | |
| 5,139,499 A | 8/1992 | Small et al. | |
| 5,246,458 A | 9/1993 | Graham | 623/17.14 |
| 5,338,297 A | 8/1994 | Kocur et al. | |
| 5,360,430 A | 11/1994 | Lin | 606/247 |
| 5,433,739 A | 7/1995 | Sluijter et al. | 607/99 |
| 5,480,401 A | 1/1996 | Navas | 616/256 |
| 5,489,307 A | 2/1996 | Kuslich et al. | |
| 5,498,265 A * | 3/1996 | Asnis et al. | 606/916 |
| 5,562,737 A | 10/1996 | Graf | 623/17.14 |
| 5,702,453 A | 12/1997 | Rabbe et al. | |
| 5,733,284 A | 3/1998 | Martin | |
| 5,743,912 A | 4/1998 | Lehille et al. | |
| 5,827,285 A | 10/1998 | Bramlet | 606/60 |
| 6,030,162 A * | 2/2000 | Huebner | 411/413 |
| 6,056,749 A | 5/2000 | Kuslich | 606/86 A |
| 6,063,121 A | 5/2000 | Xavier et al. | 623/17.15 |
| 6,086,589 A | 7/2000 | Kuslich et al. | 606/247 |
| 6,093,205 A | 7/2000 | McLeod et al. | |
| 6,125,726 A * | 10/2000 | Vendetti et al. | 81/447 |
| 6,190,413 B1 | 2/2001 | Sutcliffe | |
| 6,235,043 B1 | 5/2001 | Reiley et al. | |
| 6,258,090 B1 | 7/2001 | Jackson | |
| 6,319,254 B1 | 11/2001 | Giet et al. | |
| 6,428,576 B1 | 8/2002 | Haldimann | 623/17.16 |
| 6,440,168 B1 | 8/2002 | Cauthen | |
| 6,506,194 B1 | 1/2003 | Hajianpour | |
| 6,517,543 B1 | 2/2003 | Berrevoets et al. | |
| 6,558,386 B1 | 5/2003 | Cragg | 606/279 |
| 6,558,390 B2 | 5/2003 | Cragg | 606/80 |
| 6,575,979 B1 | 6/2003 | Cragg | 606/86 R |
| 6,582,466 B1 | 6/2003 | Gauchet | |
| 6,582,468 B1 | 6/2003 | Gauchet | |
| 6,626,943 B2 | 9/2003 | Eberlein et al. | |
| 6,652,535 B2 | 11/2003 | Kvarnstrom et al. | |
| 6,656,184 B1 | 12/2003 | White et al. | |
| 6,669,699 B2 | 12/2003 | Ralph et al. | |
| 6,682,561 B2 | 1/2004 | Songer et al. | |
| 6,692,495 B1 | 2/2004 | Zacouto | |
| 6,730,088 B2 | 5/2004 | Yeh | |
| 6,733,532 B1 | 5/2004 | Gauchet et al. | |
| 6,740,090 B1 | 5/2004 | Cragg et al. | 606/79 |
| 6,764,489 B2 | 7/2004 | Feree | |
| 6,790,210 B1 | 9/2004 | Cragg et al. | 606/80 |
| 6,821,277 B2 | 11/2004 | Teitelbaum | |
| 6,899,716 B2 | 5/2005 | Cragg | 606/86 R |
| 6,899,719 B2 | 5/2005 | Reiley et al. | |
| 6,921,403 B2 | 7/2005 | Cragg et al. | 606/86 R |
| 6,964,665 B2 | 11/2005 | Thomas et al. | |
| 7,014,633 B2 | 3/2006 | Cragg | 604/500 |
| 7,048,717 B1 | 5/2006 | Frassica | |
| 7,077,865 B2 | 7/2006 | Bao et al. | 623/17.12 |
| 7,087,058 B2 | 8/2006 | Cragg | 606/86 R |
| 7,140,281 B1 * | 11/2006 | Ruff | 81/452 |
| 7,156,877 B2 | 1/2007 | Lotz et al. | |
| 7,175,626 B2 * | 2/2007 | Neff | 606/86 A |
| 7,291,150 B2 | 11/2007 | Graf | |
| 7,361,192 B2 | 4/2008 | Doty | 623/17.12 |
| 7,419,505 B2 | 9/2008 | Fleischmann et al. | 623/17.11 |
| 7,452,359 B1 | 11/2008 | Michelson | |
| 7,473,256 B2 | 1/2009 | Assell et al. | |
| 7,491,236 B2 | 2/2009 | Cragg et al. | 623/17.11 |
| 7,547,324 B2 | 6/2009 | Cragg et al. | |
| 2001/0021852 A1 | 9/2001 | Chappius | |
| 2002/0035400 A1 | 3/2002 | Bryan et al. | |
| 2002/0068975 A1 | 6/2002 | Teitelbaum et al. | |
| 2002/0198527 A1 | 12/2002 | Muckter | 606/73 |
| 2003/0028193 A1 | 2/2003 | Weil et al. | |
| 2003/0055427 A1 | 3/2003 | Graf | 606/61 |
| 2003/0114930 A1 | 6/2003 | Lim et al. | 623/17.11 |
| 2003/0181982 A1 | 9/2003 | Kuslich | |
| 2003/0204261 A1 | 10/2003 | Eisermann et al. | |
| 2004/0083002 A1 | 4/2004 | Belef et al. | |
| 2004/0210227 A1 | 10/2004 | Trail et al. | |
| 2004/0230309 A1 | 11/2004 | DiMauro et al. | 623/17.12 |
| 2005/0043796 A1 | 2/2005 | Grant et al. | |
| 2005/0113919 A1 | 5/2005 | Cragg et al. | |
| 2005/0113929 A1 | 5/2005 | Cragg et al. | |
| 2005/0149191 A1 | 7/2005 | Cragg et al. | |
| 2005/0154390 A1 | 7/2005 | Biedermann et al. | 606/61 |
| 2005/0177167 A1 | 8/2005 | Muckter | |
| 2005/0209602 A1 | 9/2005 | Bowman et al. | 606/90 |
| 2005/0277940 A1 * | 12/2005 | Neff | 606/73 |
| 2006/0058800 A1 | 3/2006 | Ainsworth et al. | |
| 2006/0085073 A1 | 4/2006 | Raiszadeh | |
| 2006/0129147 A1 | 6/2006 | Biedermann et al. | 606/61 |
| 2006/0229609 A1 | 10/2006 | Wang | 606/61 |
| 2006/0264954 A1 | 11/2006 | Sweeney et al. | 606/73 |
| 2007/0106383 A1 | 5/2007 | Abdou | |
| 2007/0168042 A1 | 7/2007 | Hudgins et al. | |

* cited by examiner

FIG. 4
4A
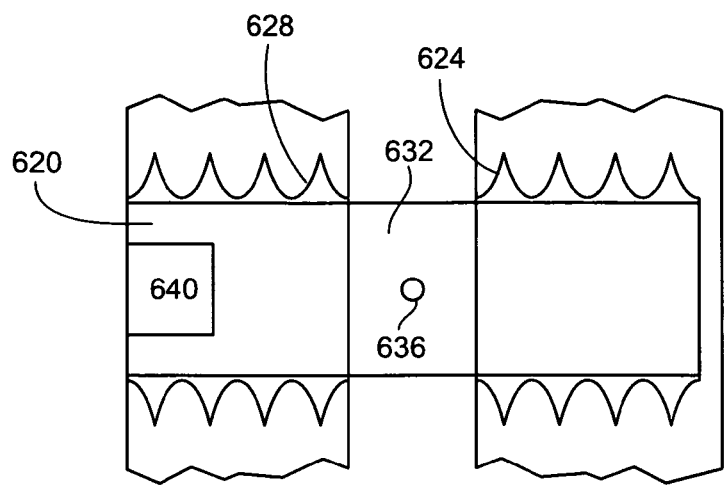
4B
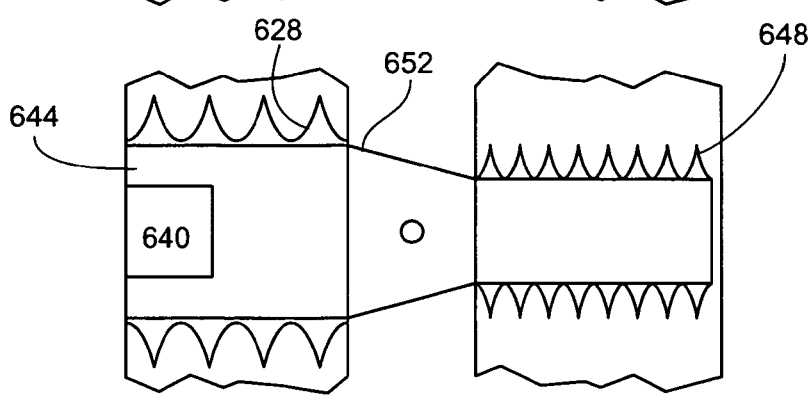
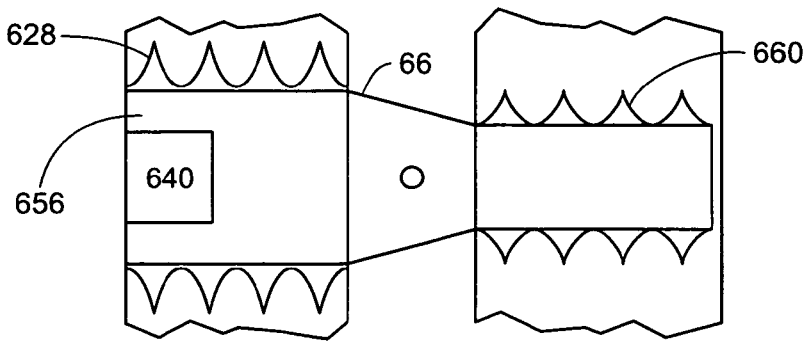
604   612   608

FIG. 5
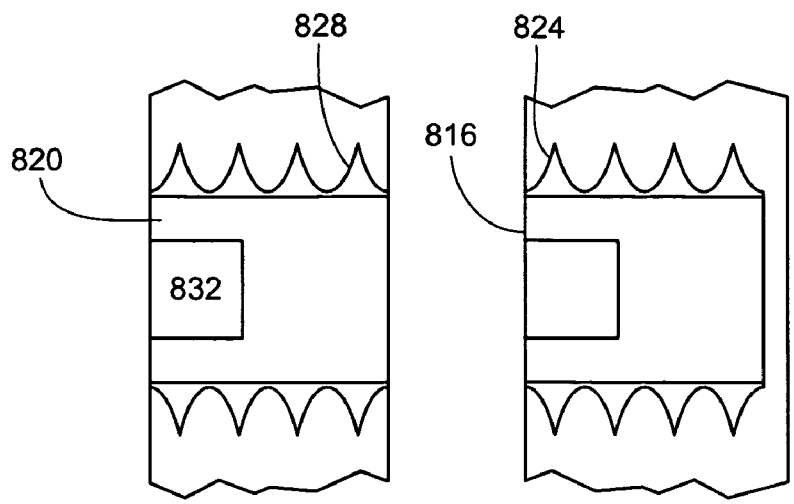
5A
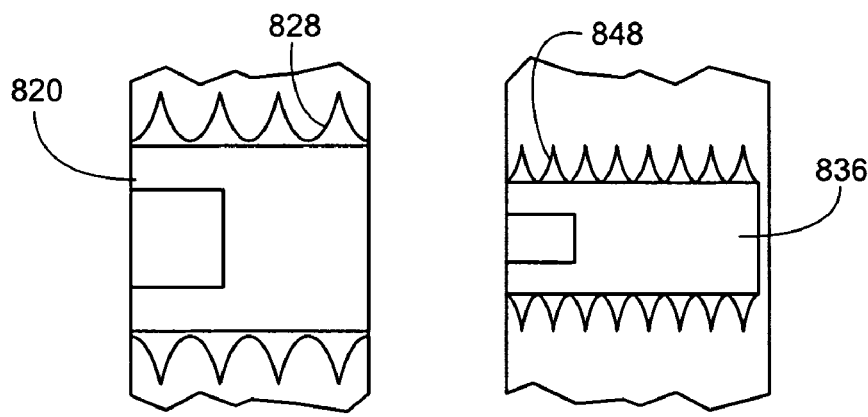
5B
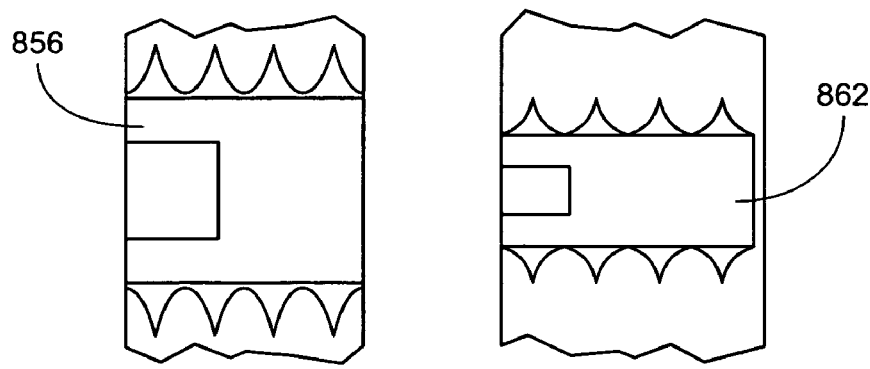
5C

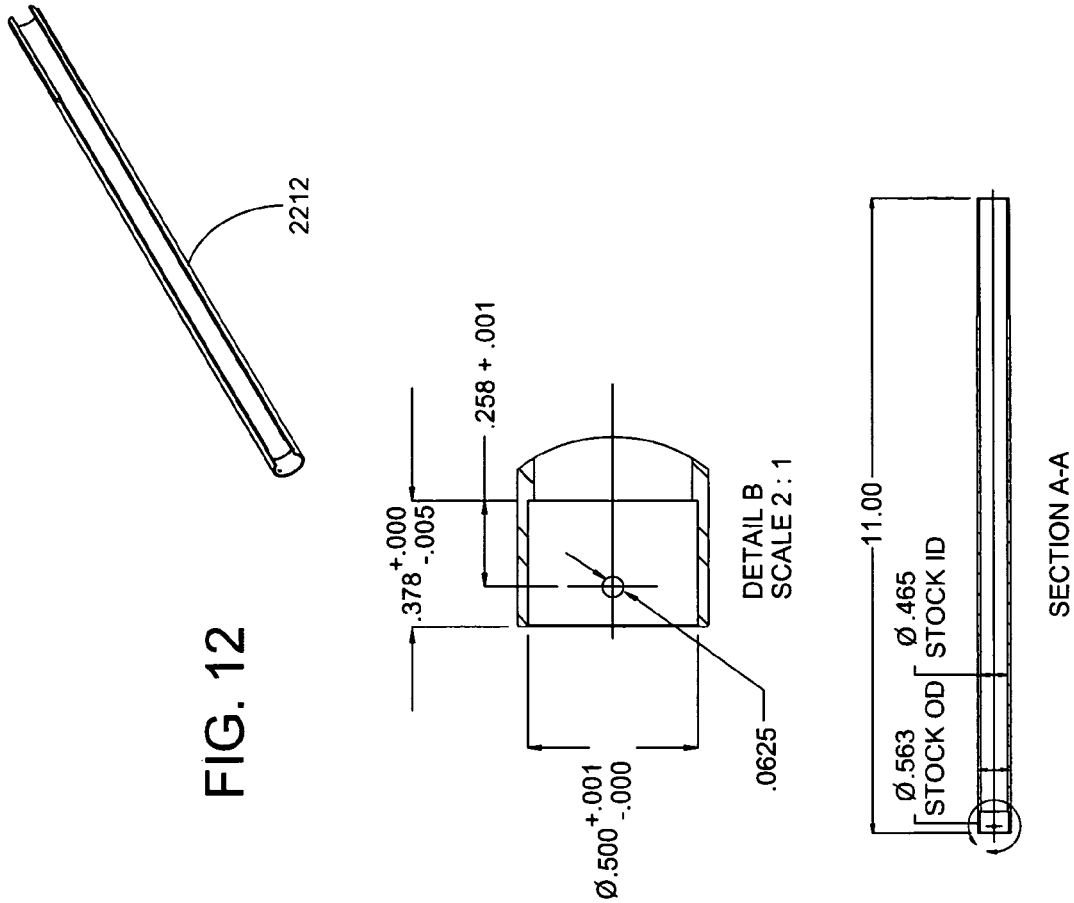
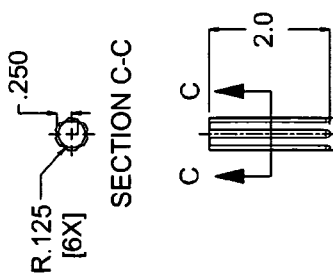
FIG. 12

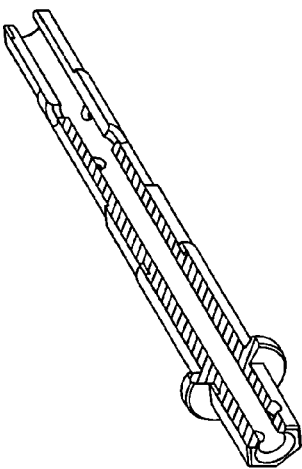
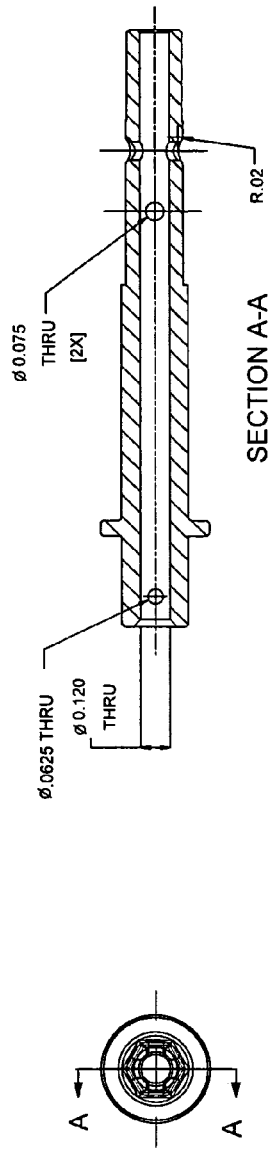
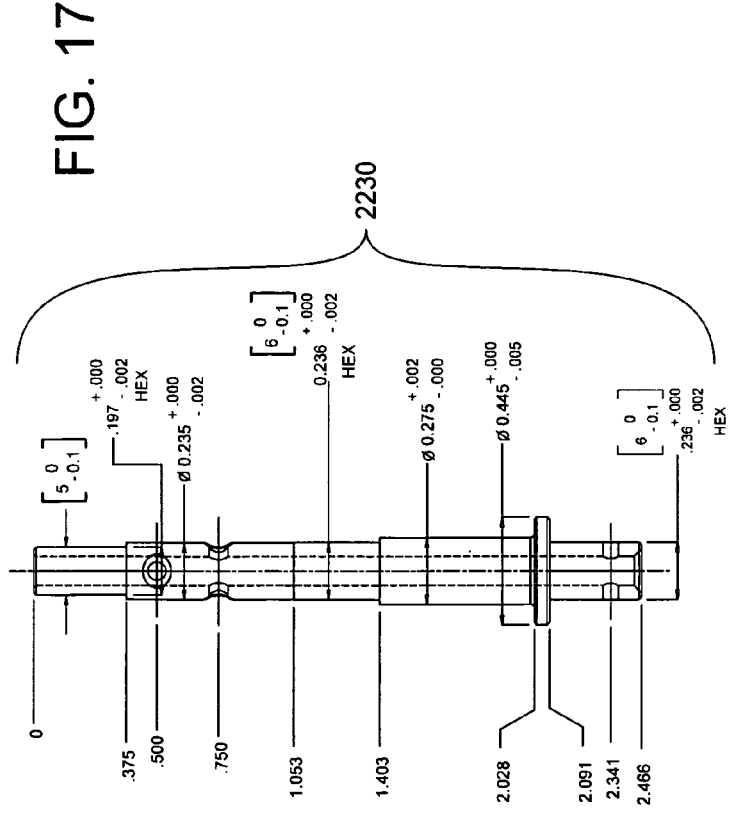
FIG. 17

FIG. 18
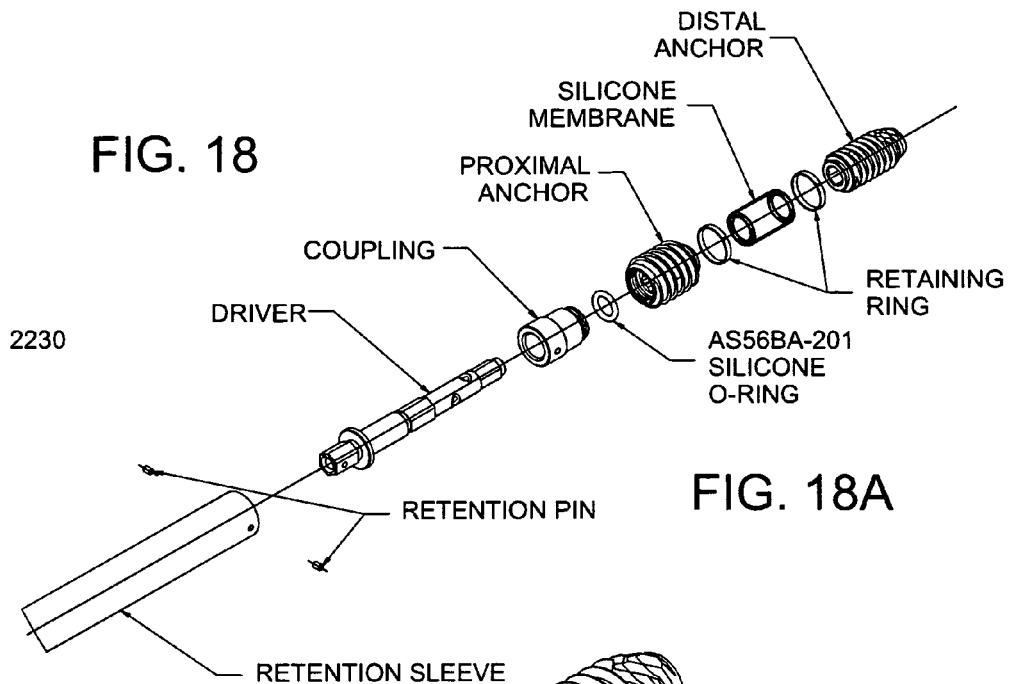
FIG. 18A
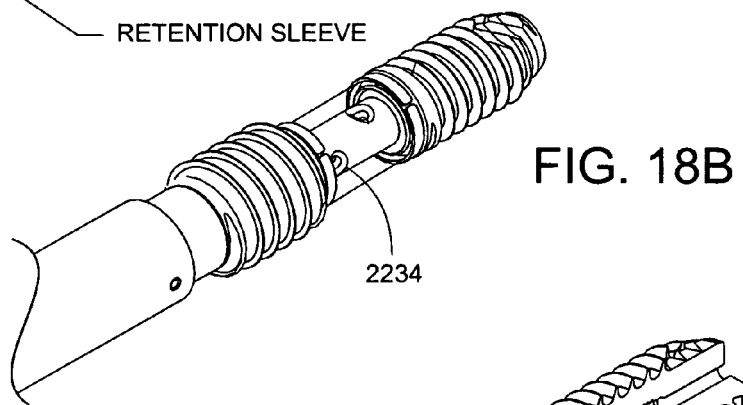
FIG. 18B
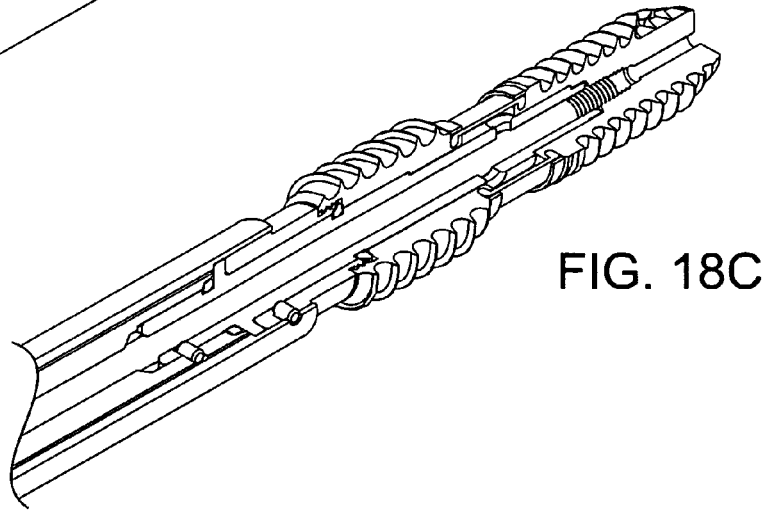
FIG. 18C

DRIVER ASSEMBLY FOR SIMULTANEOUS AXIAL DELIVERY OF SPINAL IMPLANTS

BACKGROUND OF THE INVENTION

This application claims priority and incorporates by reference a and commonly assigned U.S. Provisional Application No. 60/621,730 filed Oct. 25, 2004 for Multi-Part Assembly for Introducing Axial Implants into the Spine. This application claims priority and incorporates by reference both U.S. patent application Ser. No. 11/256,810 filed Oct. 24, 2005 for Spinal Motion Preservation Assemblies and a U.S. Provisional Application No. 60/621,148 filed Oct. 22, 2004 for Spinal Mobility Preservation Assemblies. This application claims priority and incorporates by reference four and commonly assigned U.S. patent application Ser. Nos. 10/972,184, 10/927,039, 10/972,040, and 10/972,176 all filed on Oct. 22, 2004. These four applications claim priority to two provisional application 60/558,069 filed Mar. 31, 2004 and 60/513,899 filed Oct. 23, 2003. Priority to these two provisionals is claimed through the four applications and the provisionals are incorporated by reference. This application also claims priority to and commonly assigned U.S. patent application Ser. No. 11/199,541 filed Aug. 8, 2005 and Provisional Application 60/599,989 filed Aug. 9, 2004 which is claimed as a priority document for the '541 application. Both of these applications are incorporated by reference.

This application extends the work done by TranS1 Inc. and incorporates by reference a set of United States applications, provisional applications, and issued patents including: 60/182,748 filed Feb. 16, 2000; Ser. No. 09/640,222 filed Aug. 16, 2000 (now issued as U.S. Pat. No. 6,575,979); Ser. No. 10/459,149 filed Jun. 11, 2003; Ser. No. 09/684,820 filed Oct. 10, 2000 (now issued as U.S. Pat. No. 6,558,386); Ser. No. 10/430,751 filed May 6, 2003; 60/182,748 filed Feb. 16, 2000; Ser. No. 09/782,583 filed Feb. 13, 2001 (issued as U.S. Pat. No. 6,558,390); Ser. No. 09/848,556 filed May 3, 2001; Ser. No. 10/125,771 filed Apr. 18, 2002 (issued as U.S. Pat. No. 6,899,716); Ser. No. 10/990,705 filed Nov. 17, 2004; Ser. No. 10/430,841 filed May 6, 2003; Ser. No. 09/710,369 filed Nov. 10, 2000 (issued as U.S. Pat. No. 6,740,090); Ser. No. 10/853,476 filed May 25, 2004; Ser. No. 09/709,105 filed Nov. 10, 2000 (issued as U.S. Pat. No. 6,790,210); Ser. No. 09/782,534 filed Feb. 13, 2001; application Ser. Nos. 10/971,779, 10/971,781, 10/971,731, 10/972,077, 10/971,765, 10/972,065, 10/971,775, 10/971,299, 10/971,780, all filed Oct. 22, 2004; 60/706,704 filed Aug. 9, 2005; Ser. No. 11/189,943 filed Jul. 26, 2005, Ser. No. 10/309,416 now U.S. Pat. No. 6,921,403 filed Dec. 3, 2002. While these applications have been incorporated by reference to provide additional detail it should be noted that these other applications (including those that have subsequently issued as patents) were written at an earlier time and had a different focus from the present application. Thus, to the extent that the teachings or use of terminology differs in any of these incorporated applications from the present application, the present application controls.

FIELD OF THE INVENTION

The present invention relates generally to implantable device assemblies, instrumentation systems, and methods for accessing and a spinal motion segment via a minimally-invasive trans-sacral approach (as described in U.S. Pat. No. 6,558,390 which is incorporated herein by reference) and procedures comprising the deployment of implantable components and assemblies that are anchored in bone that can be used to position, manage motion, and stabilize a vertebral motion segments in the human spine to relieve lower back pain, restore physiological function of the lumbar spine, and prevent progression or transition of degenerative disease. More specifically, the present invention generally relates to spinal motion preservation assemblies (MPA) generally introduced percutaneously through tissue to an access point on the spine in a minimally invasive, low trauma manner, to provide therapy to the spine.

BACKGROUND OF THE INVENTION

Overview

The present invention is an extension of work assigned to TranS1 Inc. with a principle place of business located in Wilmington, N.C. Much of the work is described in great detail in the many applications referenced above and incorporated by reference into this application. Accordingly, the background of the invention provided here does not repeat all of the detail provided in the earlier applications, but instead highlights how the present invention adds to this body of work.

The spinal column is a complex system of bone segments (vertebral bodies and other bone segments) which are in most cases separated from one another by discs in the intervertebral spaces (sacral vertebrae are an exception). FIG. 1 shows the various segments of a human spinal column as viewed from the side. In the context of the present invention, a "motion segment" comprises adjacent vertebrae, i.e., an inferior and a superior vertebral body, and the intervertebral disc space separating said two vertebral bodies, whether denucleated space or with intact or damaged spinal discs. Each motion segment contributes to the overall flexibility of the spine contributes to the overall ability of the spine to flex to provide support for the movement of the trunk and head.

The vertebrae of the spinal cord are conventionally subdivided into several sections. Moving from the head to the tailbone, the sections are cervical 104, thoracic 108, lumbar 112, sacral 116, and coccygeal 120. The individual vertebral bodies within the sections are identified by number starting at the vertebral body closest to the head. Of particular interest in this application are the vertebral bodies in the lumbar section and the sacral section. As the various vertebral bodies in the sacral section are usually fused together in adults, it is sufficient and perhaps more descriptive to merely refer to the sacrum rather than the individual sacral components.

It is useful to set forth some of the standard medical vocabulary before getting into a more detailed discussion of the background of the present invention. In the context of the this discussion: anterior refers to in front of the spinal column; (ventral) and posterior refers to behind the column (dorsal); cephalad means towards the patient's head (sometimes "superior"); caudal (sometimes "inferior") refers to the direction or location that is closer to the feet. As the present application contemplates accessing the various vertebral bodies and intervertebral spaces through a preferred approach that comes in from the sacrum and moves towards the head, proximal and distal are defined in context of this channel of approach. Consequently, proximal is closer to the beginning of the channel and thus towards the feet or the surgeon, distal is further from the beginning of the channel and thus towards the head, or more distant from the surgeon.

The individual motion segments within the spinal columns allow movement within constrained limits and provide protection for the spinal cord. The discs are important to bear and distribute the large forces that pass through the spinal column as a person walks, bends, lifts, or otherwise moves. Unfortunately, for a number of reasons referenced below, for some people, one or more discs in the spinal column will not operate as intended. The reasons for disc problems range from a congenital defect, disease, injury, or degeneration attributable to aging. Often when the discs are not operating properly, the gap between adjacent vertebral bodies is reduced and this causes additional problems including pain.

There are currently over 700,000 surgical procedures performed annually to treat lower back pain in the U.S. In 2004, it is conservatively estimated that there will be more than 200,000 lumbar fusions performed in the U.S., and more than 300,000 worldwide, representing approximately a $1B endeavor in an attempt to alleviate patients' pain. Approximately 60% of spinal surgery takes place in the lumbar spine, and of that portion approximately 80% involves the lower lumbar vertebrae designated as the fourth lumbar vertebra ("L4"), the fifth lumbar vertebra ("L5"), and the first sacral vertebra ("S1"). Persistent low back pain is often attributable to degeneration of the disc between L5 and S1. (See edge between the lumbar region 112 and the sacrum 116 in FIG. 1).

A range of therapies have been developed to alleviate the pain associated with disc problems. One class of solutions is to remove the failed disc and then fuse the two adjacent vertebral bodies together with a permanent but inflexible spacing, also referred to as static stabilization. As mentioned above, an estimated 300,000 fusion operations take place each year. Fusing one section together ends the ability to flex in that motion segment. While the loss of the normal physiologic disc function for a motion segment through fusion of a motion segment may be better than continuing to suffer from the pain, it would be better to alleviate the pain and yet retain all or much of the normal performance of a healthy motion segment.

Another class of therapies attempts to repair the disc so that it resumes operation with the intended intervertebral spacing and mechanical properties. One type of repair is the replacement of the original damaged disc with a prosthetic disc. This type of therapy is called by different names such as dynamic stabilization or spinal motion preservation.

The Operation of the Spine

The bodies of successive lumbar, thoracic and cervical vertebrae articulate with one another and are separated by the intervertebral spinal discs. Each spinal disc comprises a fibrous cartilage shell enclosing a central mass, the "nucleus pulposus" (or "nucleus" herein) that provides for cushioning and dampening of compressive forces to the spinal column. The shell enclosing the nucleus comprises cartilaginous endplates adhered to the opposed cortical bone endplates of the cephalad and caudal vertebral bodies and the "annulus fibrosus" (or "annulus" herein) comprising multiple layers of opposing collagen fibers running circumferentially around the nucleus pulposus and connecting the cartilaginous endplates. The natural, physiological nucleus is comprised of hydrophilic (water attracting) mucopolysacharides and fibrous strands (protein polymers). The nucleus is relatively inelastic, but the annulus can bulge outward slightly to accommodate loads axially applied to the spinal motion segment.

The intervertebral discs are anterior to the spinal canal and located between the opposed end faces or endplates of a cephalad and a caudal vertebral bodies. The inferior articular processes articulate with the superior articular processes of the next succeeding vertebra in the caudal (i.e., toward the feet or inferior) direction. Several ligaments (supraspinous, interspinous, anterior and posterior longitudinal, and the ligamenta flava) hold the vertebrae in position yet permit a limited degree of movement. The assembly of two vertebral bodies, the interposed, intervertebral, spinal disc and the attached ligaments, muscles and facet joints is referred to as a "spinal motion segment".

The relatively large vertebral bodies located in the anterior portion of the spine and the intervertebral discs provide the majority of the weight bearing support of the vertebral column. Each vertebral body has relatively strong, cortical bone layer comprising the exposed outside surface of the body, including the endplates, and weaker, cancellous bone comprising the center of the vertebral body.

The nucleus pulposus that forms the center portion of the intervertebral disc consists of 80% water that is absorbed by the proteoglycans in a healthy adult spine. With aging, the nucleus becomes less fluid and more viscous and sometimes even dehydrates and contracts (sometimes referred to as "isolated disc resorption") causing severe pain in many instances. The spinal discs serve as "dampeners" between each vertebral body that minimize the impact of movement on the spinal column, and disc degeneration, marked by a decrease in water content within the nucleus, renders discs ineffective in transferring loads to the annulus layers. In addition, the annulus tends to thicken, desiccate, and become more rigid, lessening its ability to elastically deform under load and making it susceptible to fracturing or fissuring, and one form of degeneration of the disc thus occurs when the annulus fissures or is torn. The fissure may or may not be accompanied by extrusion of nucleus material into and beyond the annulus. The fissure itself may be the sole morphological change, above and beyond generalized degenerative changes in the connective tissue of the disc, and disc fissures can nevertheless be painful and debilitating. Biochemicals contained within the nucleus are enabled to escape through the fissure and irritate nearby structures.

A fissure also may be associated with a herniation or rupture of the annulus causing the nucleus to bulge outward or extrude out through the fissure and impinge upon the spinal column or nerves (a "ruptured" or "slipped" disc). With a contained disc herniation, the nucleus may work its way partly through the annulus but is still contained within the annulus or beneath the posterior longitudinal ligament, and there are no free nucleus fragments in the spinal canal. Nevertheless, even a contained disc herniation is problematic because the outward protrusion can press on the spinal cord or on spinal nerves causing sciatica.

Another disc problem occurs when the disc bulges outward circumferentially in all directions and not just in one location. This occurs when, over time, the disc weakens bulges outward and takes on a "roll" shape. Mechanical stiffness of the joint is reduced and the spinal motion segment may become unstable, shortening the spinal cord segment. As the disc "roll" extends beyond the normal circumference, the disc height may be compromised, and foramina with nerve roots are compressed causing pain. Current treatment methods other than spinal fusion for symptomatic disc rolls and herniated discs include "laminectomy" which involves the surgical exposure of the annulus and surgical excision of the symptomatic portion of the herniated disc followed by a relatively lengthy recuperation period. In addition, osteophytes may form on the outer surface of the disc roll and further encroach on the spinal canal and foramina through which nerves pass. The cephalad vertebra may eventually settle on top of the caudal vertebra. This condition is called "lumbar spondylosis".

Various other surgical treatments that attempt to preserve the intervertebral spinal disc and to simply relieve pain include a "discectomy" or "disc decompression" to remove some or most of the interior nucleus thereby decompressing and decreasing outward pressure on the annulus. In less invasive microsurgical procedures known as "microlumbar discectomy" and "automated percutaneous lumbar discectomy", the nucleus is removed by suction through a needle laterally extended through the annulus. Although these procedures are less invasive than open surgery, they nevertheless suffer the possibility of injury to the nerve root and dural sac, perineural scar formation, re-herniation of the site of the surgery, and instability due to excess bone removal. In addition, they generally involve the perforation of the annulus.

Although damaged discs and vertebral bodies can be identified with sophisticated diagnostic imaging, existing surgical interventions and clinical outcomes are not consistently satisfactory. Furthermore, patients undergoing such fusion surgery experience significant complications and uncomfortable, prolonged convalescence. Surgical complications include disc space infection; nerve root injury; hematoma formation; instability of adjacent vertebrae, and disruption of muscle, tendons, and ligaments, for example.

Several companies are pursuing the development of prosthesis for the human spine, intended to completely replace a physiological disc, i.e., an artificial disc. In individuals where the degree of degeneration has not progressed to destruction of the annulus, rather than a total artificial disc replacement, a preferred treatment option may be to replace or augment the nucleus pulposus, involving the deployment of a prosthetic disc nucleus. As noted previously, the normal nucleus is contained within the space bounded by the bony vertebrae above and below it and the annulus fibrosus, which circumferentially surrounds it. In this way the nucleus is completely encapsulated and sealed with the only communication to the body being a fluid exchange that takes place through the bone interface with the vertebrae, known as the endplates.

The hydroscopic material comprising the physiological nucleus has an affinity for water (and swells in volume) which is sufficiently powerful to distract (i.e., elevate or "inflate") the intervertebral disc space, despite the significant physiological loads that are carried across the disc in normal activities. These forces, which range from about 0.4× to about 1.8× body weight, generate local pressure well above normal blood pressure, and the nucleus and inner annulus tissue are, in fact, effectively avascular.

The existence of the nucleus as a cushion (e.g., the nucleus is the "air" in the "tire" known as a spinal disc), and the annulus, as a flexible member, contributes to the range of motion in the normal disc. Range of motion is described in terms of degrees of freedom (i.e., translation and rotation about three orthogonal planes relative to a reference point, the instantaneous center of rotation around the vertical axis of the spine).

Distraction

Pure distraction rarely occurs and is usually a combination of tension and compression on the spinal joints depending on the direction of applied force. An example of a distraction force is therapeutic spinal traction to "unload" the spine.

In the context of the present invention, as used herein the term distraction refers procedurally to an elevation in height that increases the intervertebral disc space resulting from introduction of the motion preservation assembly or prosthetic nucleus device ("PND"), which may be achieved either in the axial deployment of the device itself, or assisted by means of a temporary distraction rod, during implantation. Temporary distraction refers to elevation of disc height by means, such as a distraction rod, which is subsequently removed but wherein the elevation is retained intra-operatively, while the patient remains prone. Thus, the device may be inserted into an elevated disc space first created by other distraction means, and thereafter physical presence and dimensionality of the inserted device is key to preserving that height space, to decompress the disc and alleviate pain caused by nerve impingement.

To date, drawbacks of currently contemplated or deployed prosthetic nucleus devices include subsidence; their tendency to extrude or migrate; to erode the bone; to degrade with time, or to fail to provide sufficient biomechanical load distribution and support. Some of these drawbacks relate to the fact that their deployment typically involves a virtually complete discectomy of the disc achieved by instruments introduced laterally through the patient's body to the disc site and manipulated to cut away or drill lateral holes through the disc and adjoining cortical bone. The endplates of the vertebral bodies, which comprise very hard cortical bone and help to give the vertebral bodies needed strength, are usually weakened or destroyed during the drilling. The vertebral endplates are special cartilage structures that surround the top and bottom of each vertebra and are in direct contact with the disc. They are important to the nutrition of the disc because they allow the passage of nutrients and water into the disc. If these structures are injured, it can lead to deterioration of the disc and altered disc function. Not only do the large laterally drilled hole or holes compromise the integrity of the vertebral bodies, but the spinal cord can be injured if they are drilled too posterior.

Alternatively, current devices are sometimes deployed through a surgically created or enlarged hole in the annulus. The annulus fibrosus consists of tough, thick collagen fibers. The collagen fibers which comprise the annulus fibrosus are arranged in concentric, alternating layers. Intra-layer orientation of these fibers is parallel, however, each alternating (i.e., interlayer) layers' collagen fibers are oriented obliquely (~120). This oblique orientation allows the annulus to resist forces in both vertical and horizontal directions. Axial compression of a disc results in increased pressure in the disc space. This pressure is transferred to the annulus in the form of loads (stresses) perpendicular to the wall of the annulus. With applied stress, these fibrous layers are put in tension and the angle from horizontal decreases to better resist the load, i.e., the annulus works to resist these perpendicular stresses by transferring the loads around the circumference of the annulus (Hoop Stress). Vertical tension resists bending and distraction (flexion and extension). Horizontal tension resists rotation and sliding (i.e., twisting). While the vertical components of the annulus' layers enable the disc to withstand forward and backward bending well, only half of the horizontal fibers of the annulus are engaged during a rotational movement. In general, the disc is more susceptible to injury during a twisting motion, deriving its primary protection during rotation from the posterior facet joints; however, this risk is even greater if and when the annulus is compromised.

Moreover, annulus disruption will remain post-operatively, and present a pathway for device extrusion and migration in addition to compromising the physiological biomechanics of the disc structure. Other devices, in an attempt to provide sufficient mechanical integrity to withstand the stresses to which they will be subjected, are configured to be so firm, stiff, and inflexible that they tend to erode the bone or become imbedded, over time, in the vertebral bodies, a phenomenon known as "subsidence", sometimes also termed "telescoping". The result of subsidence is that the effective length of the vertebral column is shortened, which can subsequently cause damage to the nerve root and nerves that pass between the two adjacent vertebrae.

SUMMARY OF THE DISCLOSURE

Tools used in the deployment of spinal implant assemblies such as spinal mobility preservation assemblies are disclosed.

These tools assist in the three steps which are commonly part of the deployment process although some deployments may not require all three steps and some methods of deployment perform two of the steps at the same time.

Generally, the assemblies may be inserted axially within the spine, following either partial or complete nucleectomy and through a cannula that is docked against the sacrum, into a surgically de-nucleated disc space, from said access point across a treatment zone. In one aspect of the invention, prosthetic or augmentation materials are introduced, through at least one vertebral body or into at least one disc space. The introduction of the spinal motion preservation assemblies is accomplished without the need to surgically create or deleteriously enlarge an existing hole in the annulus fibrosus of the disc, and their deployment therapeutically preserves the physiological function of natural disc structures.

In one aspect of the invention, risks associated with implant expulsion, migration, or subsidence (that are inherently less for the motion preservation assemblies of the present invention) may be even further mitigated by retention means, e.g., by external, self-tapping threads configured to distribute stress evenly over a large surface area, that engage the vertebral body and secure (i.e., anchor) the implant assemblies therein.

The screw threads are typical of "cancellous" type bone threads known in the art. The threads are typically cut with generally flat faces on the flights of the thread with the most flat of the faces oriented in the direction of the applied load. In one embodiment, the thread profile generally comprises deep flights with an asymmetric thread form, which provides the advantage of improved weight bearing and load distribution. Threads are formed on root portions and extend as continuous threads from the trailing end to the leading end of the respective threaded sections. The screw threads include multiple revolutions that are spaced apart along the roots by inter-thread spacings. The proximal component and distal component threads are like-handed (i.e. the threads turn in the same direction) so that both screw threads are right-handed or so that both are left-handed.

The self-tapping threads may or may not be configured to assist in distraction of adjacent vertebral bodies within a motion segment, i.e., may or may not be configured with distal and proximal components (anchored in superior and inferior vertebral bodies, respectively) with differential thread pitches, and wherein the distal anchor has a major diameter that is less than that of the proximal anchor. Clockwise rotation of embodiments configured with right-handed threads (i.e., differential pitch and major diameters as just described) advances assemblies axially and distracts the superior and inferior vertebral bodies within a motion segment relative one to the other.

In the context of this application, "dynamic" refers to non-static devices with an inherent ability to allow mobility by enabling or facilitating forces or load bearing that assist or substitute for physiological structures that are otherwise compromised, weakened or absent. The mobility preservation assemblies (MPA) introduced by an axial trans-sacral approach provide dynamic stabilization (DS) across a progression-of-treatment interventions for treating symptomatic discogenic pain, ranging from treatment in patients where little degeneration or collapse is evident radio-graphically, to those for whom prosthetic nucleus devices or total disc replacements are indicated. For example, a prosthetic nucleus (PN) would be indicated in patients with a greater degree of degeneration and loss of disc height but not to the stage where advanced annular break-down is present. A prosthetic nucleus would go beyond dynamic stabilization by including an aggressive nucleectomy and subsequent filling of the de-nucleated space with an appropriate material. Here, the goal is to restore disc height and motion. Total disc replacement (TDR) is generally indicated with more advanced disease than with a prosthetic nucleus but where some annular function remains. The motion preservation assemblies can serve as prosthetic disc replacements (PDR) that are much less invasive (in terms of deployment) than traditional total disc replacements, and are configured so as to augment, preserve, restore, and/or manage the physiological function according to the intervention indicated. In general, the axial motion preservation assemblies are preferably configured as devices with an aspect ratio of greater than 1, i.e., the device dimension in the axial vertebral plane is greater than the device dimension in any orthogonal direction to that axial plane in close proximity to the physiological instantaneous center of axial rotation, and are deployed in an orientation in approximately the line of principal compressive stress, and placed at approximately the center of rotation vis á vis a human disc motion segment.

BRIEF DESCRIPTION OF THE FIGURES

FIG. 4 is a series of drawings describing situations with a dual anchor rod implanted in a motion segment.

FIG. 5 illustrates a situation where driving the proximal component will not rotate the distal component.

FIGS. 8-16 provide details on components within the dual anchor driver assembly of FIGS. 6-7.

FIG. 17 shows a dual hex head driver with apertures.

FIG. 18 shows an exploded diagram and a loaded driver assembly with a dual hex head driver.

DETAILED DESCRIPTION

The present invention will now be described more fully hereinafter with reference to accompanying drawings in order to disclose selected illustrative embodiments. This invention may, however, be embodied in many different forms and should not be construed as limited to the embodiments set forth herein; rather these embodiments are provided so that the disclosure can be thorough and complete, and as part of the effort to convey the scope of the invention to those skilled in the art. Like numbers refer to like elements throughout.

Axial Trans-Sacral Access

The present invention contemplates the use of the axial trans-sacral access to the lumbo-sacral spine. The axial trans-sacral access method illustrated in FIG. 2, eliminates the need for muscular dissection and other invasive steps associated with traditional spinal surgery while allowing for the design and deployment of new and improved instruments and therapeutic interventions, including stabilization, motion preservation, and fixation devices/fusion systems across a progression-of-treatment in intervention.

Figure 2A:
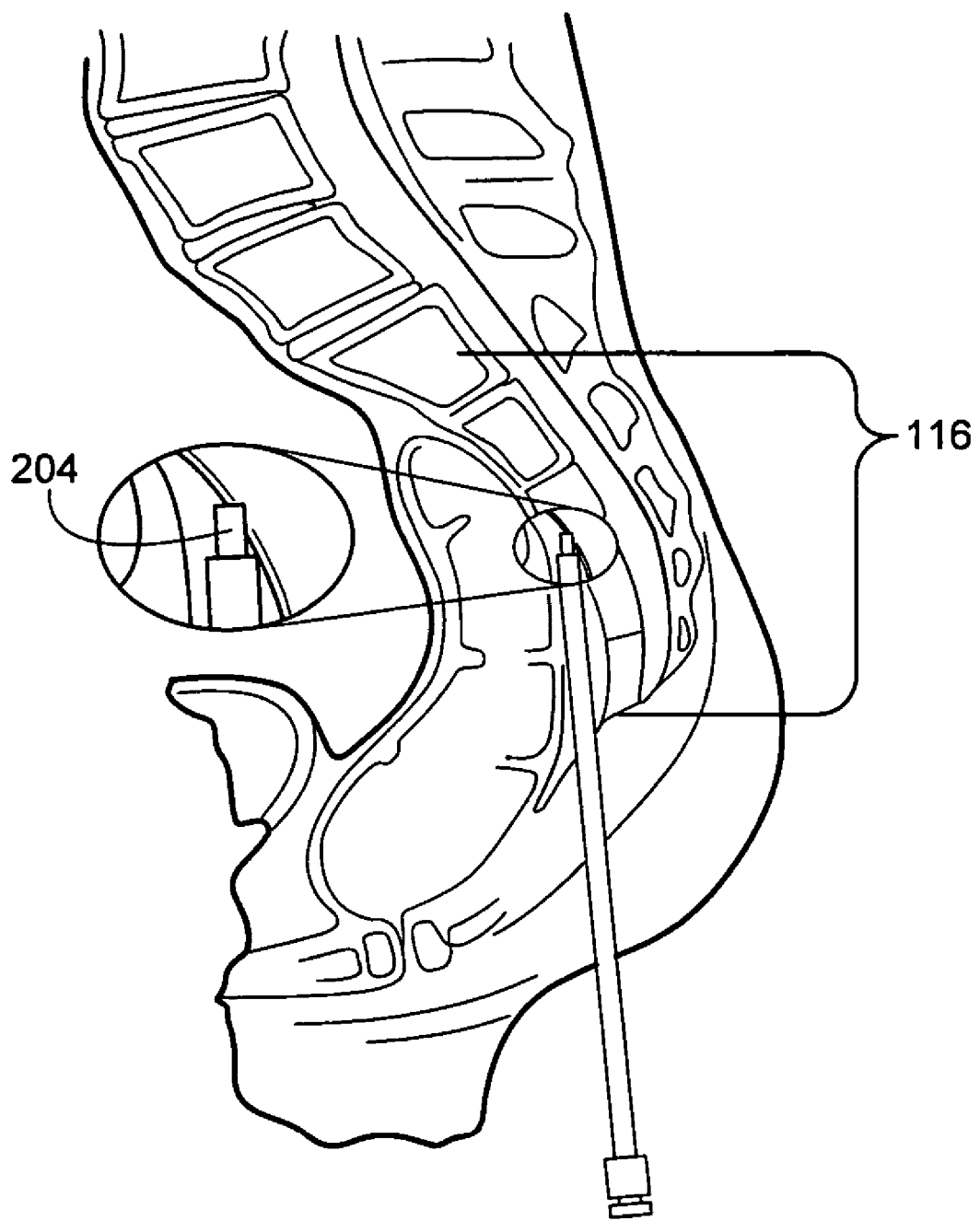
FIG. 2 illustrates an anterior axial trans-sacral access method of creating an axial channel in the spine which can be used to prepare an axial channel in the spine for use with the present invention.
Figure 2B:
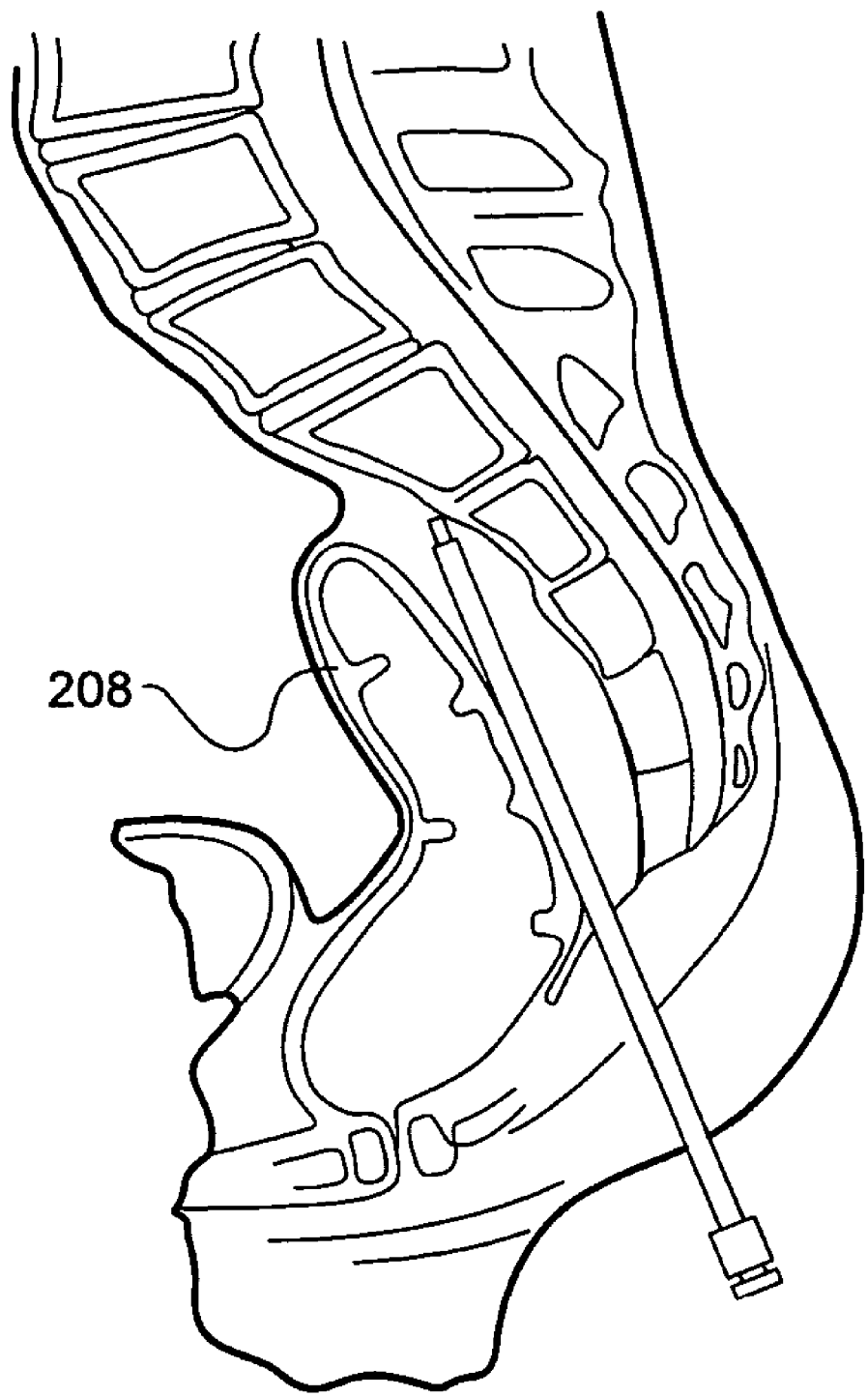
Figure 2C:
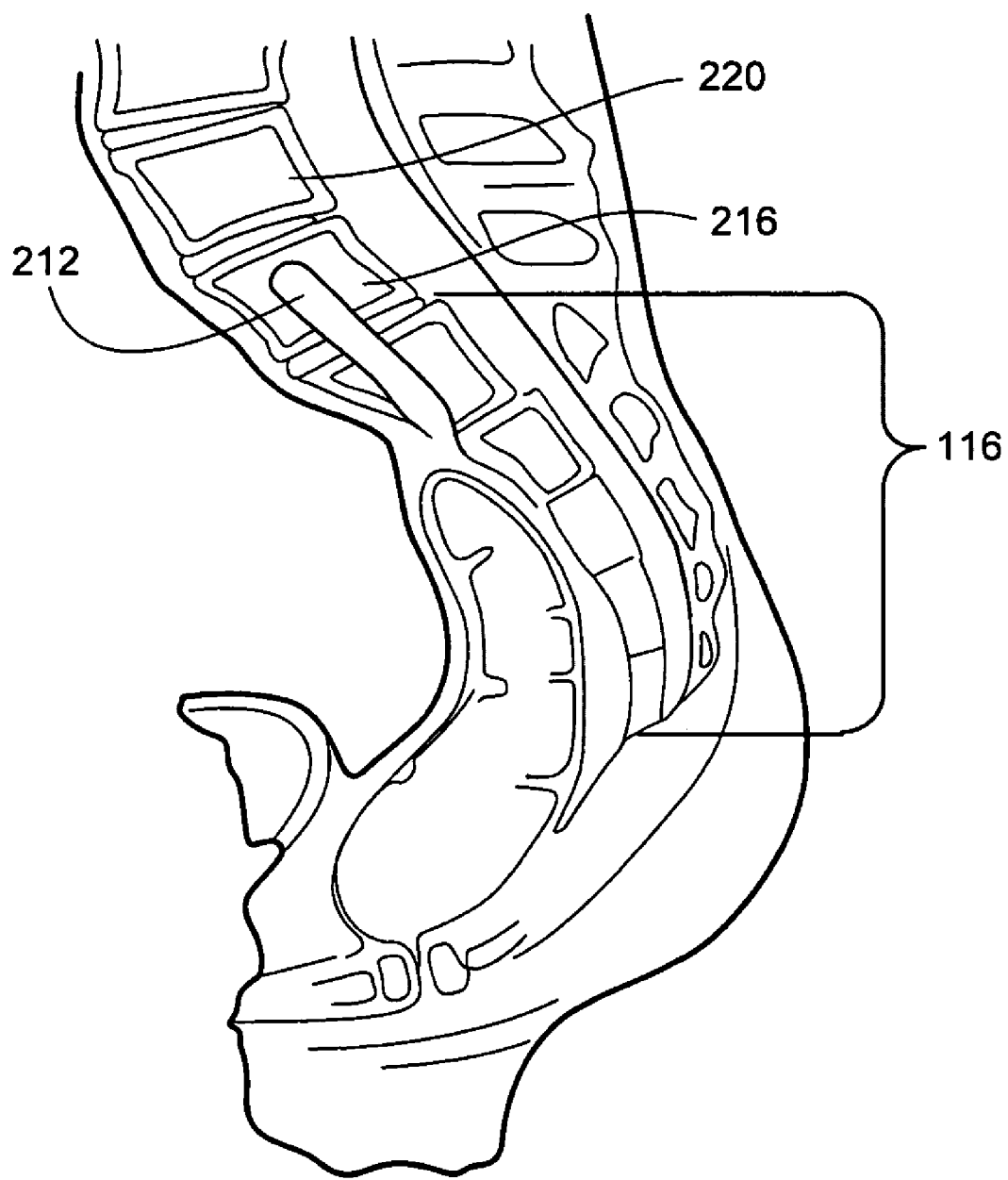

FIG. 2 provides an introductory overview of the process with FIGS. 2A and 2B showing the process of "walking" a blunt tip stylet 204 up the anterior face of the sacrum 116 to the desired position on the sacrum 116 while monitored on a fluoroscope (not shown). This process moves the rectum 208 out of the way so that a straight path is established for the subsequent steps. FIG. 2C illustrates a representative axial trans-sacral channel 212 established through the sacrum 116, the L5/sacrum intervertebral space, the L5 vertebra 216, the L4/L5 intervertebral space, and into the L4 vertebra 220. If therapy is not being provided to the L4/L5 motion segment then the channel would end in L5 rather than extend into L4.

The discussion of FIG. 2 is provided to provide context for the present invention. Previous applications (some now issued as United States patents) assigned to TranS1, Inc. have included a description of an alternative access method that is a posterior trans-sacral axial spinal approach rather than an anterior trans-sacral axial spinal approach. (See e.g. U.S. Pat. No. 6,558,386 for Axial Spinal Implant and Method and Apparatus for Implanting an Axial Spinal Implant Within the Vertebrae of the Spine as this patent describes the anterior trans-sacral axial approach illustrated in FIG. 2 and is incorporated by reference in its entirety.) The teachings of the present invention can be utilized with an axial trans-sacral channel.

A brief overview of this method of accessing the spinal region to receive therapy is useful to provide context for the present invention. As shown in FIG. 2A, a pre-sacral approach through percutaneous anterior track towards sacral target, through which trans-sacral axial bore will be made and channel extended distally for subsequent advancement of multi-level axial spinal stabilization assemblies. An anterior, pre-sacral, percutaneous tract extends through the "pre-sacral space" anterior to the sacrum. The pre-sacral, percutaneous tract is preferably used to introduce instrumentation to access and prepare (e.g., by drilling a bore in the distal/cephalad direction through one or more lumbar vertebral bodies and intervening discs). "Percutaneous" in this context simply means through the skin and to the posterior or anterior target point, as in transcutaneous or transdermal, without implying any particular procedure from other medical arts. However, percutaneous is distinct from a surgical access, and the percutaneous opening in the skin is preferably minimized so that it is less than 4 cm across, preferably less than 2 cm, and, in certain applications, less than 1 cm across. The percutaneous pathway is generally axially aligned with the bore extending from the respective anterior or posterior target point through at least one sacral vertebral body and one or more lumbar vertebral body in the cephalad direction as visualized by radiographic or fluoroscopic equipment. More specifically, as shown in FIG. 2b, the lumbar spine is accessed via a small skin puncture adjacent to the tip of the coccyx bone. The pre-sacral space is entered, using standard percutaneous technique, and the introducer assembly with the stylet's blunt tip serving as a dilator is placed through the paracoccygeal entry site. Once the tip of the stylet is through the facial layer, the blunt tip is rotated back against the anterior face of the sacrum and "walked" to the desired position on the sacrum under fluoroscopic guidance. Once the target site has been accessed and risk of soft tissue damage mitigated, the blunt-tipped stylet is removed and a guide pin, or wire, is safely introduced through the guide pin introducer tube, and "tapped in". The guide pin establishes the trajectory for placement of subsequent bone dilators and sheath through which a twist drill is introduced creating an axial bore track, the lumen of which is extended distally. The guide pin maintains the axial alignment of access & preparation tools as well as the alignment of cannulated spinal stabilization devices and assemblies, of larger diameter than the bore track, that are subsequently introduced over a 23" long, 0.090" diameter guide pin and through an exchange cannula for deployment of within the vertebral column, as described at least in part in co-pending and commonly assigned U.S. patent application Ser. Nos. 10/972,065; 10/971,779; 10/971,781; 10/971,731; 10/972,077; 10/971,765; 10/971,775; 10/972,299; and 10/971,780, all of which were filed on Oct. 22, 2004, and in and commonly assigned U.S. Provisional Patent Application 60/706,704, filed Aug. 9, 2005, and all of which are incorporated by reference herein in their entirety.

Context

In order to provide context to the present invention it is useful to briefly describe the major components of a an implanted spinal implant assembly of the type described in greater detail in pending U.S. patent application No. 11/256,810 filed Oct. 24, 2005 for Spinal Motion Preservation Assemblies. The specifics provided in FIG. 3 are provided in order to provide context for the problems addressed by the present invention and are not to be construed as a limitation on the uses of the present invention.

Figure 1:
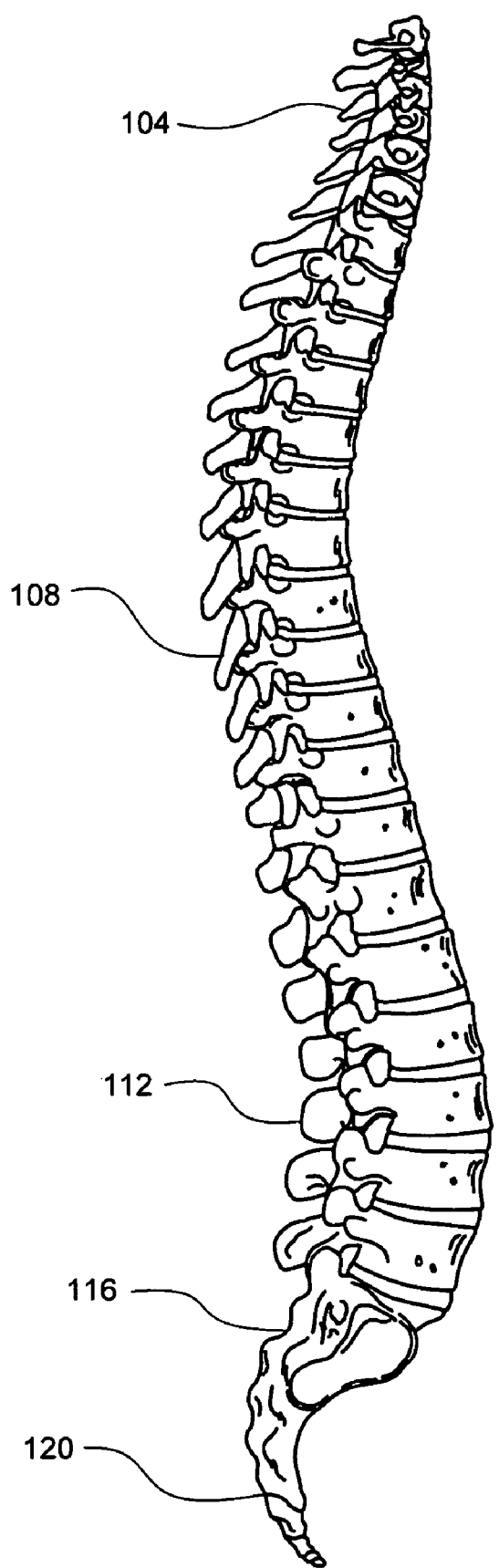
FIG. 1 identifies the sections of a human spine.
Figure 3:
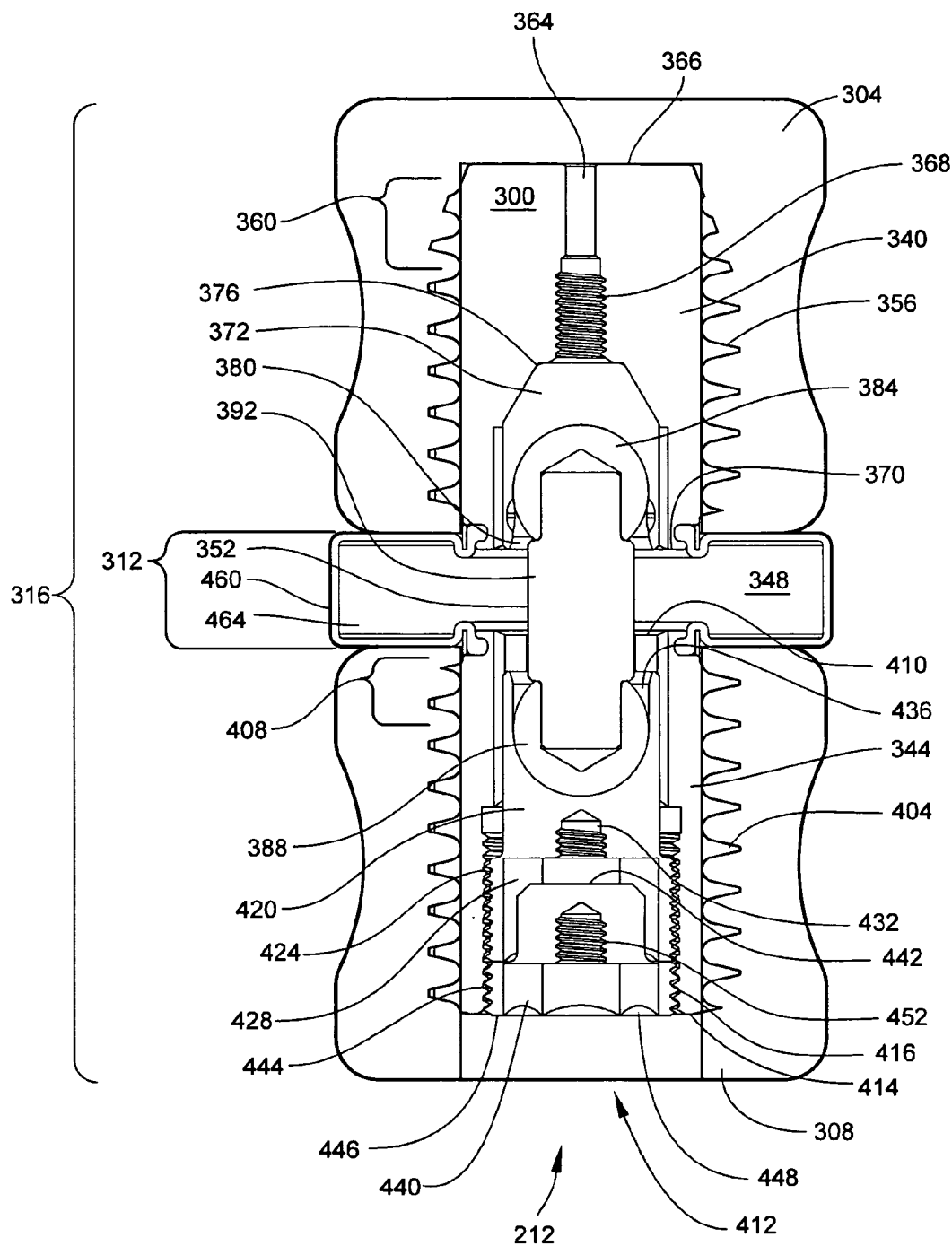
FIG. 3 illustrates an implanted motion preservation assembly 300 in a spinal motion segment.

FIG. 3 illustrates an implanted motion preservation assembly 300. This motion preservation assembly 300 is implanted into a distal vertebral body 304 and a proximal vertebral body 308 and extends across an intervertebral disc space 312. The motion preservation assembly 300 would be placed in a previously prepared axial channel 212. Collectively, the distal vertebral body 304, the proximal vertebral body 308 and the intervertebral disc space 312 form a motion segment 316. The drawings of the vertebral bodies are not intended to convey anatomical details of the spinal components but to illustrate the placement of the assembled motion preservation assembly 300. One mapping of the components illustrated in FIG. 3 onto a spine would be for the distal vertebral body to be the L5 vertebral body 216 (See FIG. 2) at the caudal end of the lumbar section 112 (See FIG. 1) and the proximal vertebral body 308 would be the sacrum 116 (See FIG. 1). Alternatively, the motion segment could be more cephalad (and thus more distal to the surgeon) such as the L4/L5 vertebral bodies 220, 216 (See FIG. 2).

The major components of the motion preservation assembly 300 include the distal component (anchored in the superior, or distal vertebral body, herein also sometimes referred to as distal bone anchor) 340, proximal component (anchored in the inferior, or proximal vertebral body, herein also sometimes referred to as proximal bone anchor) 344, prosthetic nucleus 348 (generally including outer membrane 460), and a pivot 352. The outer membrane can be comprised of an elastomeric material, e.g. silicone rubber, such as that obtained from Nusil Silicone Technology located in Carpeneria, Calif., exhibiting elongation of between about 500% and about 1500% and most preferably about 1000% and having a wall thickness of 0.220 inches.

The distal bone anchor 340 shown in FIG. 3 has a set of external threads 356. Advantageously, the set of external threads 356 can include a chip breaker section 360 at the distal end of the distal bone anchor to facilitate the starting of cutting a thread path into the distal vertebral body 304. A chip breaker is a discontinuity in the thread that allows chips to break off as the thread path is cut. The axial channel 212 is created into the distal vertebral body 304, with the diameter of the axial channel 212 at the distal vertebral body 304 approximately equal to the minor diameter of the set of external threads 356.

The distal bone anchor 340 has a cavity 364 running from the distal face 366 of the distal bone anchor 340 to the proximal face 370 of the distal bone anchor 340. In this context, a face is the three dimensional surface of the part as viewed from that side, akin to the six three dimensional faces of die from a pair of dice. The cavity 364 is not of uniform cross section and serves several purposes. The distal end of the cavity 364 illustrates that the cavity can be used to allow the distal bone anchor 340 to be deployed over a guide wire. The cavity 364 includes an internal threaded section 368 which can be engaged by a driver, retention or extraction tool as described below. The cavity 364 in the distal bone anchor 340 shown in FIG. 3 contains a distal pivot cup 372 in a corresponding cup section 376 of the cavity 364.

The distal pivot cup 372 in turn has a cavity 380 which serves as a bearing surface for the distal end 384 of the pivot 352.

The pivot 352 shown in FIG. 3 has the distal end 384 referenced above and a proximal end 388 which in this embodiment are configured as substantially spherical components integral with the pivot body 392.

The proximal bone anchor 344 has a set of external threads 404 including a lead-in section 408. The proximal bone anchor 344 has a cavity 412 that runs from the distal face 410 of the proximal bone anchor 344 to the proximal face 414 of the proximal bone anchor 344. The cavity 412 is not uniform in cross section. A portion of the cavity 412 has a set of internal threads 416. Preferably, the pitch of the set of internal thread 416 will be relatively fine (perhaps 16 threads per inch up to 64 threads per inch). In the particular motion preservation assembly shown in FIG. 3, the proximal bone anchor cavity 412 contains a proximal pivot cup 420 that has a set of external threads 424 that engage with the set of internal threads 416 to allow torque from a driver (not shown) imparted to a driver engagement section 428 to rotate the proximal pivot cup 420 relative to the proximal bone anchor 344 to axially (distally) advance the proximal pivot cup 420. One can appreciate that axially advancing the proximal pivot cup 420 will cause the proximal pivot cup 420 to contact the pivot 352 and cause the pivot 352 to contact the distal pivot cup 372. After these components are in contact, further axial advancement of the proximal pivot cup 420 will cause the axial movement of the distal bone anchor 340 (and the distal vertebral body 304 engaged with the distal bone anchor 340) relative to the proximal bone anchor 344 (and the proximal vertebral body 308 engaged with the proximal bone anchor 344). This movement of one vertebral body away from another vertebral body causes a distraction of the intervertebral disc space between the two vertebral bodies.

Note that the distraction that can be achieved by rotation of the proximal pivot cup 420 is preferably used as an adjustment to alter the distribution of loading between the pivot and the prosthetic nucleus component of the motion preservation assembly. The primary means for achieving distraction is by means of the distraction and insertion tool as will be described below.

Returning to FIG. 3, the driver engagement section 428 could be configured among any one of many types of ways to impart torque with a driver. A female hex socket is a suitable choice. The proximal pivot cup 420 shown in FIG. 3 includes a threaded cavity 432 which can be engaged with a driver or extraction tool. The proximal pivot cup 420 includes a distal cavity 436 that serves as a bearing surface for the proximal end 388 of the pivot 352.

The cavity 412 in the proximal bone anchor 344 also includes a jam nut 440 with a distal end 442 and a proximal end 446. The jam nut 440 has set of external threads 444 adapted to engage with the set of internal threads. The jam nut 440 also has a driver engagement section 448 that is adapted to receive torque imparted by a corresponding driver such as a male hex driver. The torque input can cause the jam nut 440 to axially (distally) advance until it makes contact with the proximal pivot cup 420. The jam nut 440 shown in FIG. 3 also includes a threaded cavity 452 which can be used by a driver or extraction tool.

The prosthetic nucleus 348 includes an outer membrane 460 and prosthetic nucleus material 464. As outer membrane 460 is filled with prosthetic nucleus material 464, the outer membrane 460 expands to conformably contact the inferior endplate of the distal vertebral body 304, the superior endplate of the proximal vertebral body 308, and the inner wall of the annulus fibrosus (not shown) which collectively define the boundaries of an intervertebral disc space 312.

Preferred prosthetic nucleus materials and systems comprise biomedical grade silicone elastomer e.g. silicone rubber, such as that obtained from Nusil Silicone Technology located in Carpeneria, Calif. or hydrogels or blends thereof (e.g., hydrogel/hydrogel, or hydrogel/elastomer). Cross-linked hyaluronic acid, such as is available from Fidia Corporation in Italy, is an example of a suitable material, however, many natural and man-made hydrogels or blends thereof may be configured to achieve similar properties without inflammatory response, such as those disclosed and described in and commonly assigned United States patent applications referenced above, and in detail in particular in U.S. Provisional Patent Application 60/599,989 filed Aug. 9, 2004, and 60/558,069 filed Mar. 31, 2004, each of which are incorporated in their entirety into this disclosure by reference Distraction of the Motion Segment Though Use of Dissimilar Thread Pitches Previously filed applications assigned to Trans1, Inc. have described a process for imposing a distraction on a motion segment (to move the two vertebral bodies away from each other along the z axis). For example see U.S. Pat. No. 6,921,403 for Method and Apparatus for Spinal Distraction and Fusion. Thus, when a threaded rod with a distal threaded section of a first, finer thread pitch engages with a distal vertebral body (after passing through a bore in the proximal vertebral body larger than the major diameter of the threads on the distal threaded section) and a proximal, coarser threaded section on the same threaded rod engages with a proximal vertebral body, the rotation of the two threaded sections with different thread pitches causes the distal finer pitched threads to advance into the distal vertebral body slower than the coarser threads advance into the proximal vertebral body. The net effect is that the engagement of the two threaded sections with the two vertebral bodies causes the two vertebral bodies to move apart.

Driving Two Threaded Implant Components

The implant components such as distal bone anchor 340 and proximal bone anchor 344 shown in FIG. 3 are much more than bone anchors but they do serve the function of anchoring the spinal implant assembly into vertebral bodies.

As part of preparing the axial channel 212, the distal vertebral body is bored through to create a bore hole approximately the size of the proximal bone anchor 344 less the external threads 404, or in other words approximately the size of the minor diameter of the external threads 404 of the proximal bone anchor 344. Likewise the axial channel 212 is extended at least partway into the distal vertebral body 304 and the bore size is approximately the size of the minor diameter of the external threads 356 on the distal bone anchor 340.

In the case of FIG. 3, the minor diameters of both these sets of external threads are the same. In some spinal implant assemblies the major diameter of the external threads of the distal bone anchor is less than the minor diameter of the external threads on the proximal bone anchor so that the distal bone anchor can pass through the bore in the proximal vertebral body without leaving a helical thread cut in the proximal vertebral body.

FIG. 4 illustrates the various combinations of thread and bore sizes starting with a single rod with two threaded sections, one for the distal vertebral body and one for the proximal vertebral body. FIG. 4, like other Figures in this application, serves to introduce and illustrate concepts relevant to the present invention and is not intended to convey specific dimensional proportions.

FIG. 4 shows a series of proximal vertebral bodies 604 and distal vertebral bodies 608 with intervertebral disc spaces 612 located between the two vertebral bodies. Each pair of vertebral bodies as a dual anchor rod implanted. FIG. 4A shows a dual anchor rod 620 with two threaded sections of the same diameter and pitch. As the threads 624 for the distal vertebral body 608 were driven through the proximal vertebral body 604, a helical thread path was cut into the proximal vertebral body 604. When the leading portion of threads 628 reach the proximal vertebral body 604, it is preferable that these threads 628 use the same helical thread path previously cut by the threads 624. Failure to do so results in cross threading which either makes it difficult to drive the dual anchor rod 620 or results in cutting new helical path into the proximal vertebral body which means that the vertebral body has undergone more mechanical damage than necessary (or both happen). Avoidance of cross threading is not difficult in this situation as the pitch of the threads 624 is the same as the pitch of the thread 628 so that the two sets of threads can be placed relative to one another as if it was one continuous set of threads. Thus, avoiding cross threading as the two sets of threads are rigidly connected by a waist section 632. Waist section 632 lies between the two threaded sections and in particular, is located in the intervertebral disc space 612. As described in earlier applications incorporated by reference, the waist section 632 can include apertures 636 in fluid communication with a central cavity in the dual anchor rod 620 so that therapeutic materials such as bone paste used in fusion therapy can be delivered.

A single driver engagement section 640 such as a female hex socket can be engaged with a corresponding driver to rotate, axially advance, and implant the dual anchor rod 620 into engagement with both the proximal vertebral body 604 and the distal vertebral body 608.

FIG. 4B shows a dual anchor rod 644 where the set of threads 648 for engagement with the distal vertebral body 608, have a major diameter that is slightly less than the minor diameter of the set of threads 628 so that the set of thread 648 do not cut a spiral thread cut into the proximal vertebral body 604 as these threads are axially advanced towards a bore in the distal vertebral body 608. The dual anchor rod 644 has a single driver engagement section 640 which rotates both sets of threads 628 and 648 as these sections are connected by waist 652. As described in the material incorporated by reference, the use of threads with a finer pitch in the distal vertebral body 608 and threads of a coarser pitch in the proximal vertebral body 604 imposes a distraction to increase the distance between the proximal vertebral body 604 and the distal vertebral body 608 to increase the size of the intervertebral disc space 612.

The decrease in major diameter between thread set 628 and thread set 648 has the disadvantage of decreasing the amount of interaction between the thread set 648 and the distal vertebral body 608. This decrease in major diameter is necessary when the pitches are not the same in order to avoid creating a helical thread path that the subsequent thread set 628 would be unable to follow due to the difference in thread pitch.

Thus, the example shown in FIG. 4C is not commonly found as having a dual anchor rod 656 with thread sections 628 and 660 with different major diameters but the same thread pitch connected by waist 664 does not have the advantages of either dual anchor rod 620 or dual anchor rod 644.

Some spinal implant assemblies, including spinal implant assemblies disclosed in and commonly assigned U.S. patent Ser. No. 11/256,810 filed Oct. 24, 2005 for Spinal Motion Preservation Assemblies (incorporated by reference herein) disclose assemblies where the component that is implanted in the distal vertebral body 608 is not rigidly connected to the component implanted in the proximal vertebral body 604. The two components may be connected at point of implantation into the vertebral bodies by a flexible membrane 460 (See FIG. 3) that will be expanded with injected prosthetic nucleus material to form a prosthetic nucleus 348 (FIG. 3), however, the connection afforded by the flexible membrane 460 is not sufficiently rigid to control the relative positions of the two separate components. Thus for example FIG. 5A illustrates that when using a distal component 816 and a proximal component 820 with the external thread sets 824 and 828 having the same major diameter and pitch, a driver engaged with driver engagement section 832 cannot impart torque to the distal component 816. Thus, there is a need for a driver that can deliver a distal component to a distal vertebral body and a proximal component to a proximal vertebral body and to do so while avoiding the problems associated with cross threading without forcing the use of a distal component of reduced cross sectional area.

While the example given to illustrate the problem references a flexible membrane that is expanded to form the outer boundary of a prosthetic nucleus membrane, the problem would extend to other integral connections between the distal and proximal component that are insufficient to allow torque applied at driver engagement section 832 to drive the thread set 824 into the distal vertebral body 608.

For example, the previous applications and issued patents for assignee, TranS1 Inc. include teachings regarding the formation of a prosthetic nucleus using an injected barrier sealant material to seal the interior surfaces of the intervertebral disc space before injection prosthetic nucleus material. Components delivered as part of the process of a therapy using a barrier sealant material in lieu of a flexible membrane would, by definition, not be connected by a flexible membrane.

FIG. 5B illustrates the case where distraction of the motion segment is desired and the chosen method of distraction is the use of dissimilar thread pitches between the thread set 848 on the distal component 836 and thread set 828 on the proximal component 820. Again there is a need to impart torque to not only a driver engagement section 820 on proximal component 820 but also to convey torque to distal component 836. Even if these two components were not connected by an intermediate though non-rigid component, sequential implantation would not be an option as there is a need to inject prosthetic nucleus material into the expanded intervertebral disc space 612 while the distraction force if present so that the injected prosthetic nucleus material can cure in the expanded intervertebral disc space and help to maintain the distraction as the tool implementing the distraction is removed.

FIG. 5C is offered for completeness, but it will be less common to use two separate components 856 and 862 that have different major diameters for their thread sets but have the same thread pitch.

Thus, the prior art did not provide a suitable solution for use in the axial delivery of two components to two adjacent vertebral bodies nor did the prior art provide a suitable solution for the process of axial delivery of two components to two adjacent vertebral bodies combined with an imposed distraction of the vertebral bodies to be maintained by the insertion of prosthetic nucleus material.

EXAMPLE A

Figure 6A:
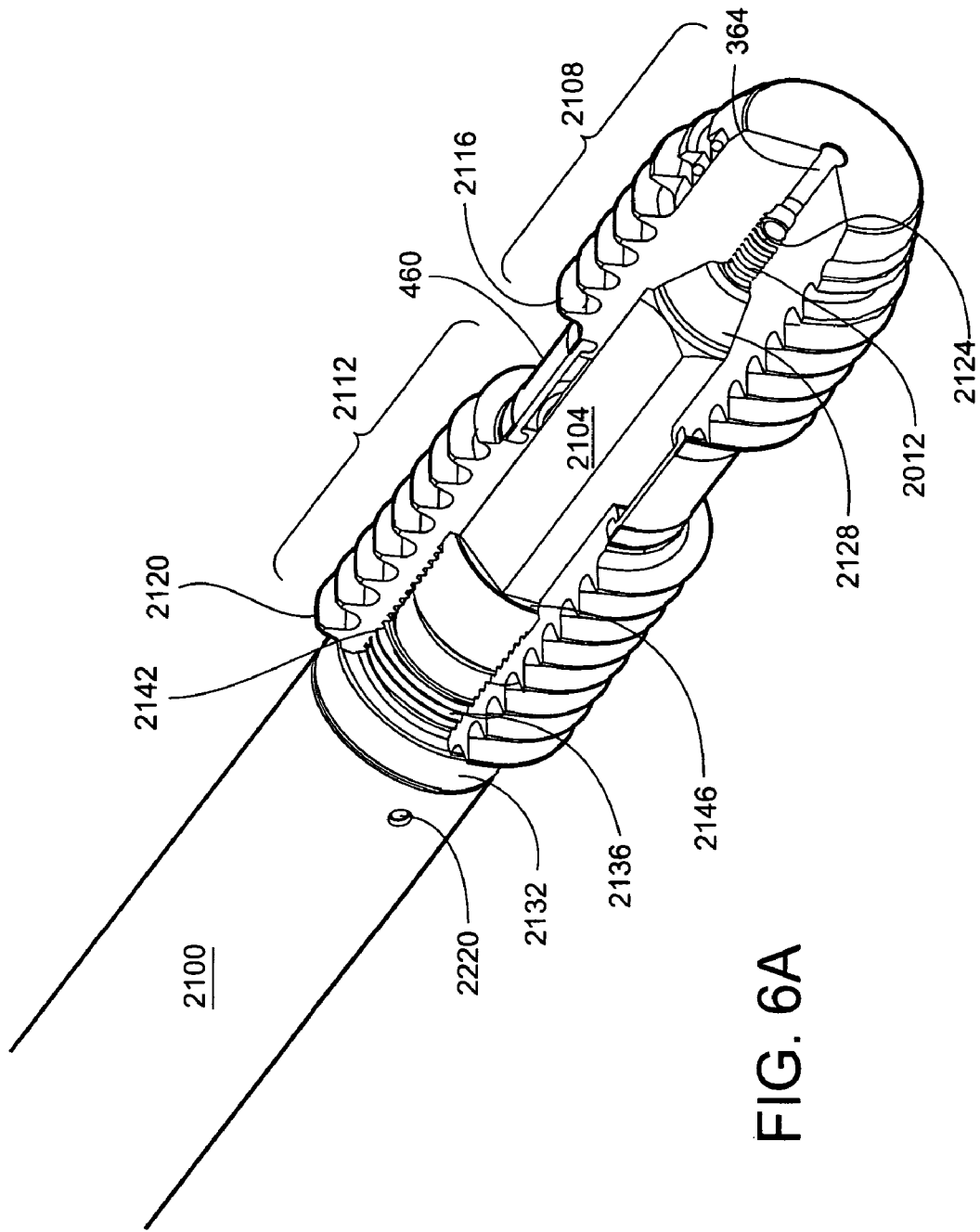
FIG. 6 shows a dual anchor driver assembly with an elongated polygonal torque driver.

One solution to the above-identified short comings in the prior art is shown in FIG. 6. FIG. 6A shows an enlarged portion of a loaded dual anchor driver assembly 2100 in a perspective view with a quarter round removed to expose the interaction of components. The dual anchor driver assembly 2100 uses a polygonal torque driver 2104 to simultaneously engage a distal bone anchor 2108 and a proximal bone anchor 2112. These bone anchors have external threaded sections (2116 and 2120) that have the same minor diameter, the same major diameter, the same pitch, and the same handedness. In order to avoid cross threading the helical thread cut left by distal anchor external threads 2116 in the proximal vertebral body as the proximal anchor external threads 2120 are rotated into the proximal vertebral body, the delivery of the two bone anchors must be timed. Having control over the relative position of the bone anchors during the rotation and axial advancement of the bone anchors makes this possible. Here the control is provided by A) the action of retention rod 2012 engaging with internal threads 2124 of distal anchor 2108 to pull the distal anchor 2108 to seat it on the distal tip 2128 of the polygonal torque driver 2104 and B) the action of proximal anchor retention coupler 2132 engaging a set of external threads 2136 with internal threads 2142 of proximal anchor 2112 to seat the proximal anchor 2112 on a shoulder 2146 polygonal torque driver 2104. Both retention rod 2012 and proximal anchor retention coupler 2132 are connected to dual anchor driver 2100 such that each can rotate relative to the polygonal torque driver 2104.

Figure 6B:
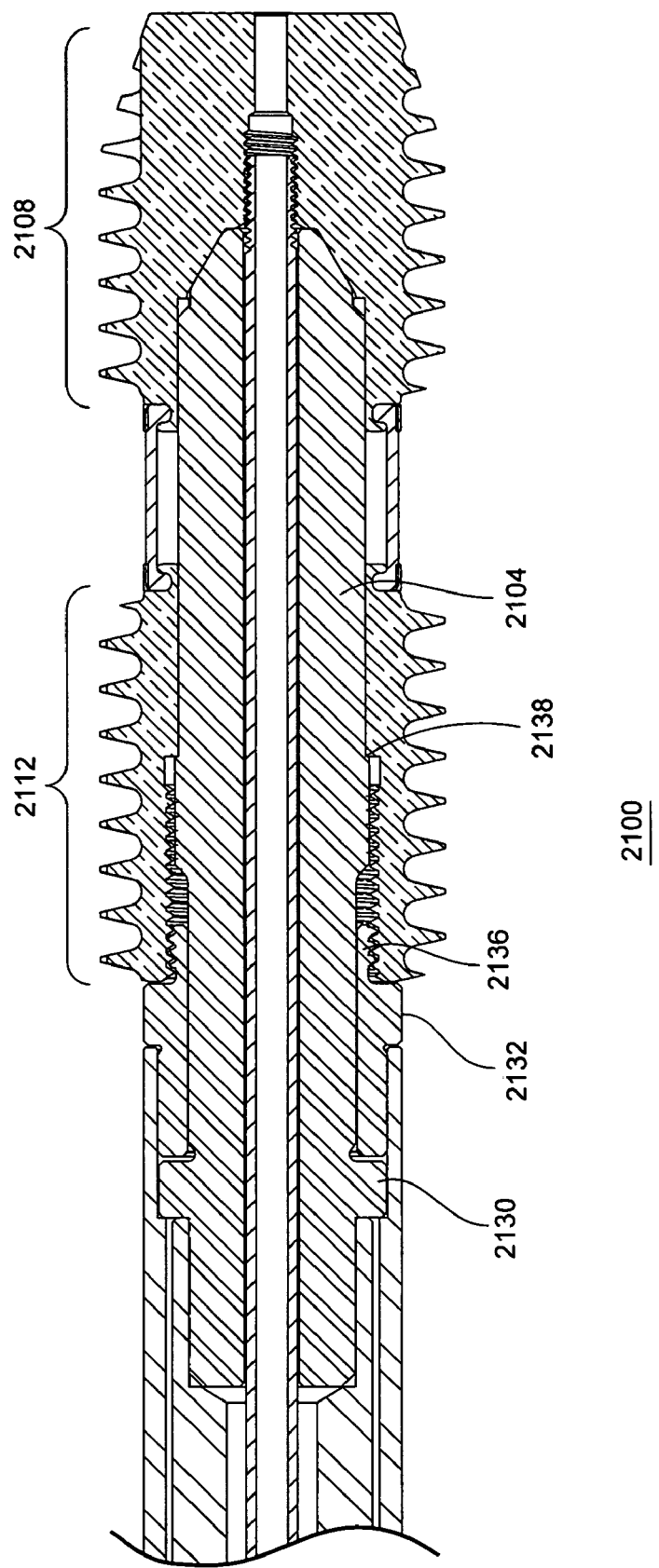

FIG. 6B shows a cross section of the dual anchor driver 2100 including shoulder 2138 of the polygonal torque driver 2104 that contacts the proximal anchor 2112 and shows the engagement of the flange 2130 with the other components in the dual anchor driver assembly 2100.

One of skill in the art will recognize that while a hexagonal polygon is commonly used as a torque driver, other polygons could be used such as triangular, square, pentagonal, octagonal and so on. More complex shapes such as stars or non symmetric shapes could be used but a simple polygon is adequate.

Figure 7:
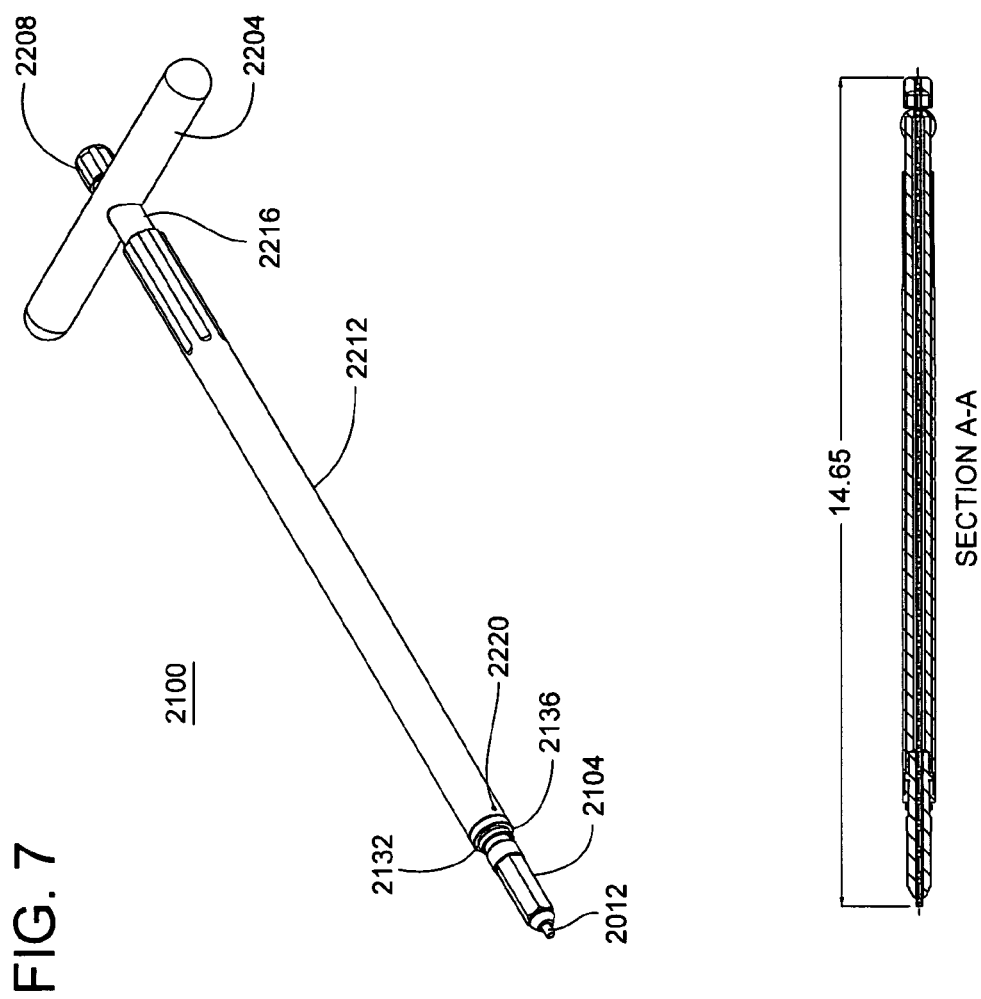
FIG. 7 shows the complete dual anchor driver assembly of FIG. 6.
Figure 8:
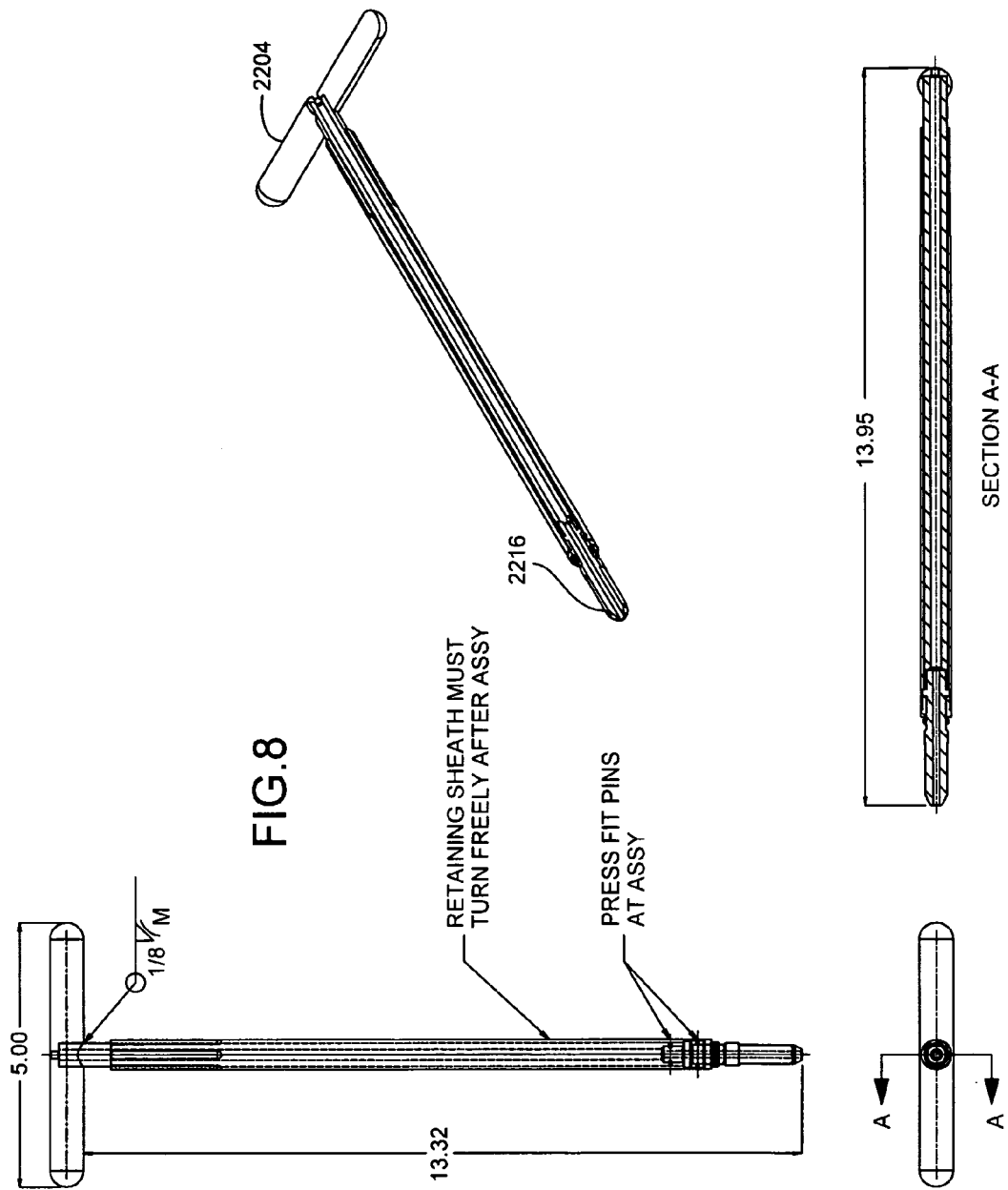
Figure 9:
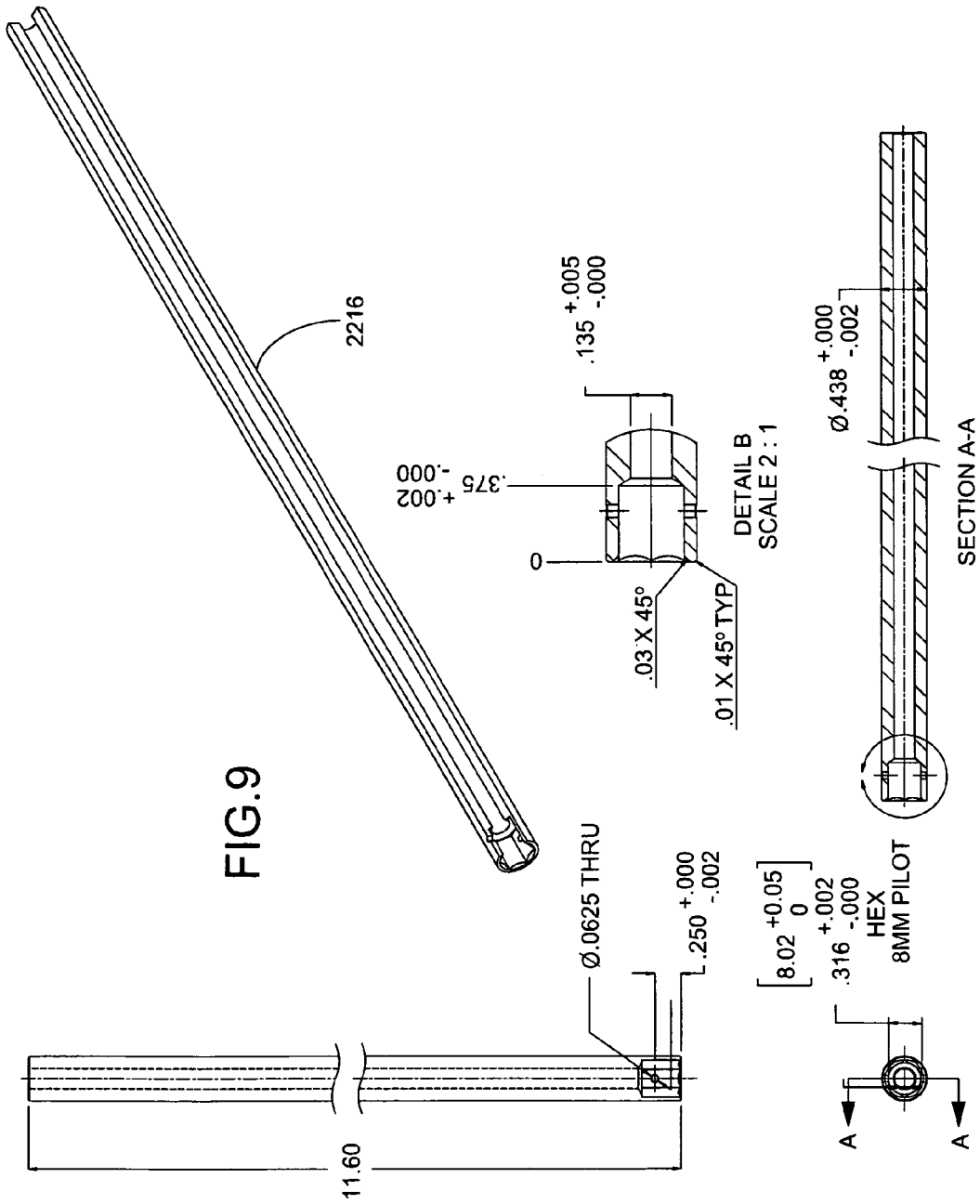

FIG. 7 shows dual anchor driver assembly 2100 with handle 2204. Rotating the handle rotates the driver shaft 2216 including the polygonal torque driver 2104. The distal component 2108 can be threadedly engaged by rotation of thread on retention rod 2012 by rotating the retention rod knob 2208. This causes the retention rod to rotate relative to the polygonal torque driver 2014.

Rotation of external sheath 2212 causes threaded engagement by external threads 2036 on proximal anchor retention coupler 2032 with corresponding threads on the proximal anchor. The sheath 2211 and attached proximal anchor retention coupler 2032 can rotate relative to the polygonal torque driver 2104. Retention pins 2220 retain the proximal anchor coupler 2032 to the sheath 2212.

A set of detailed drawings of the various components that comprise a dual anchor driver 2100 of the type shown in FIG. 7 are provided in FIGS. 8-16 and should be self-explanatory of those of skill in the art. (Detailed drawings not provided of retainer pins as these details should be discernable from the other drawings).

EXAMPLE B

Figure 10:
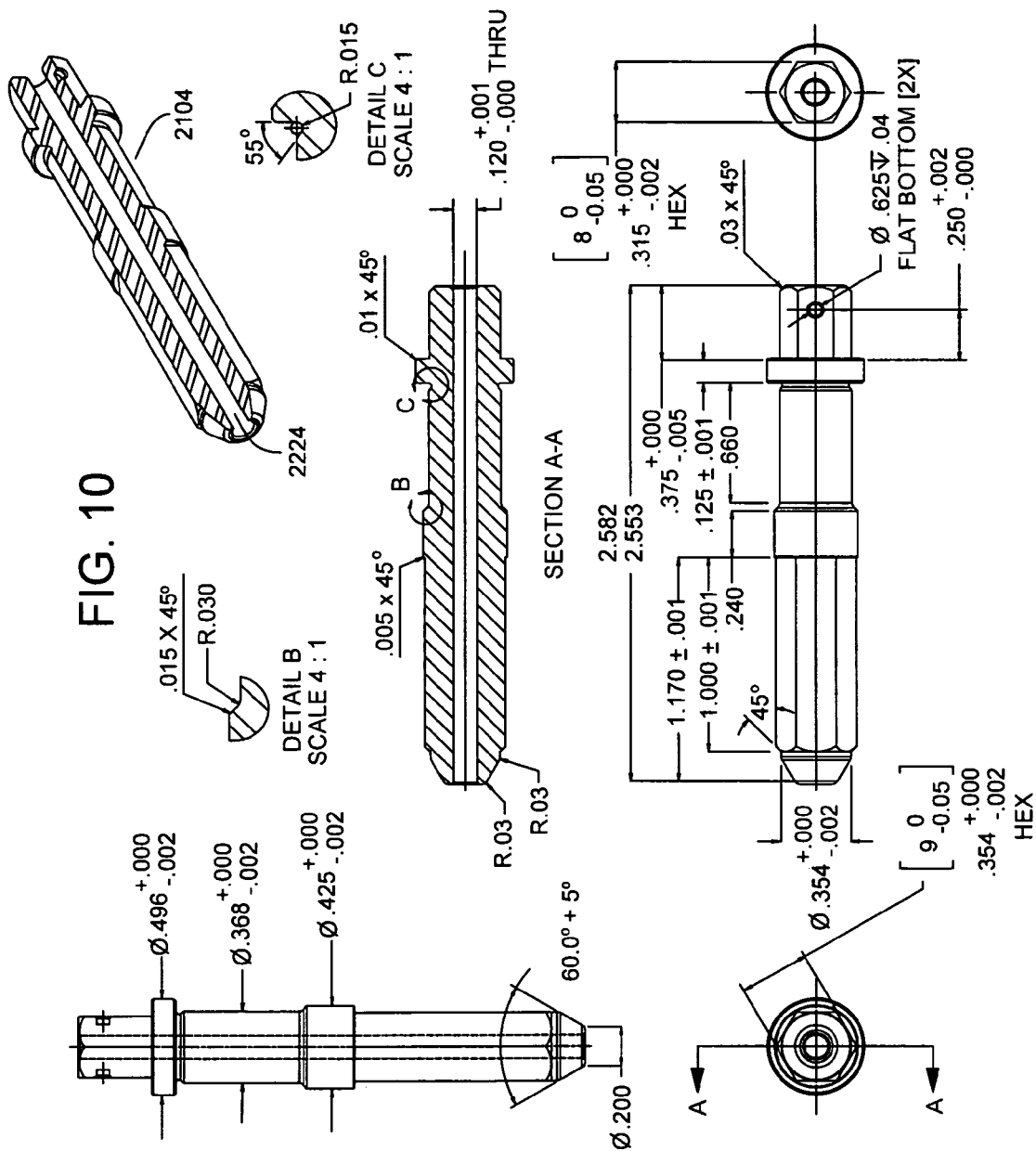
Figure 11:
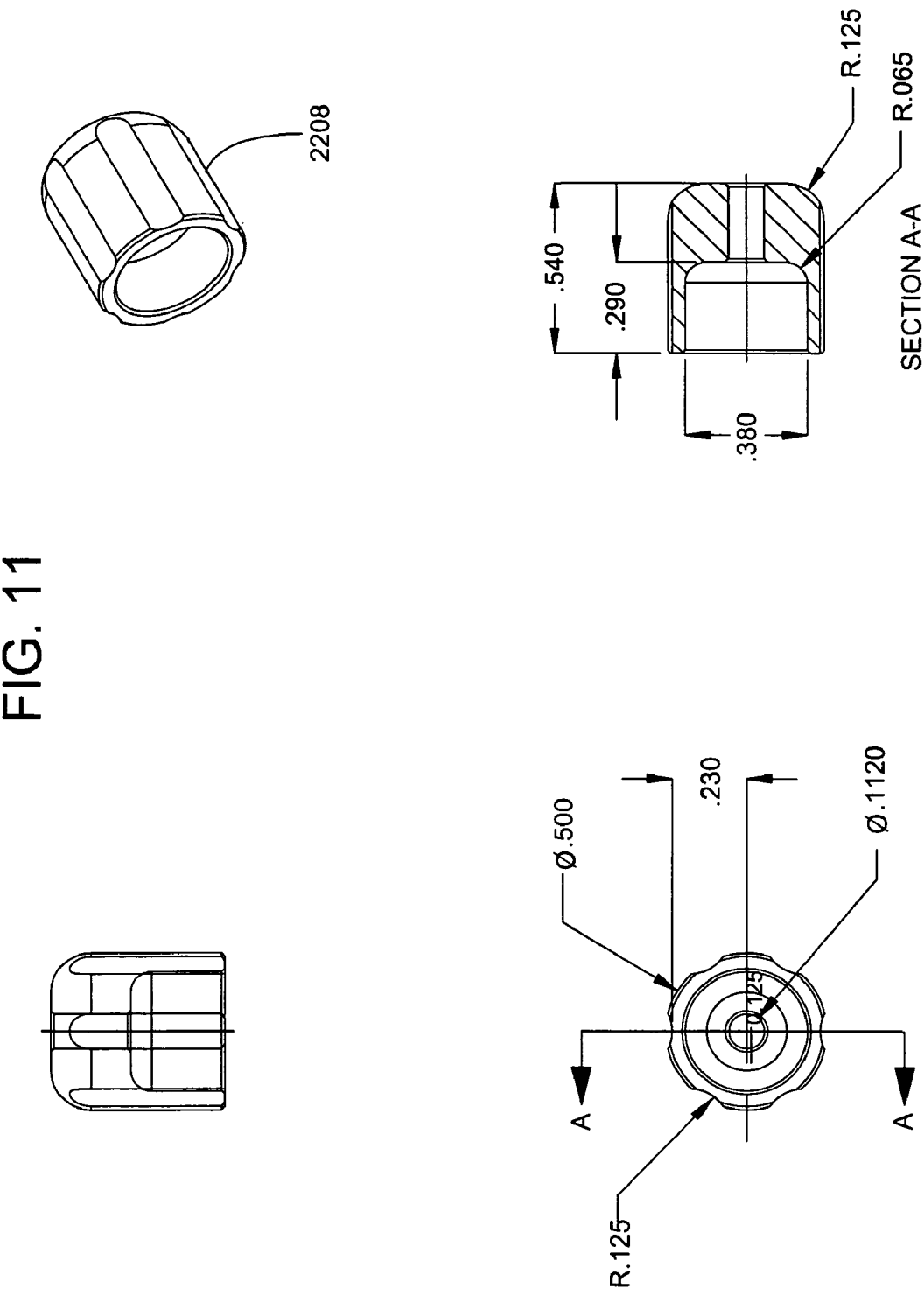
Figure 13:
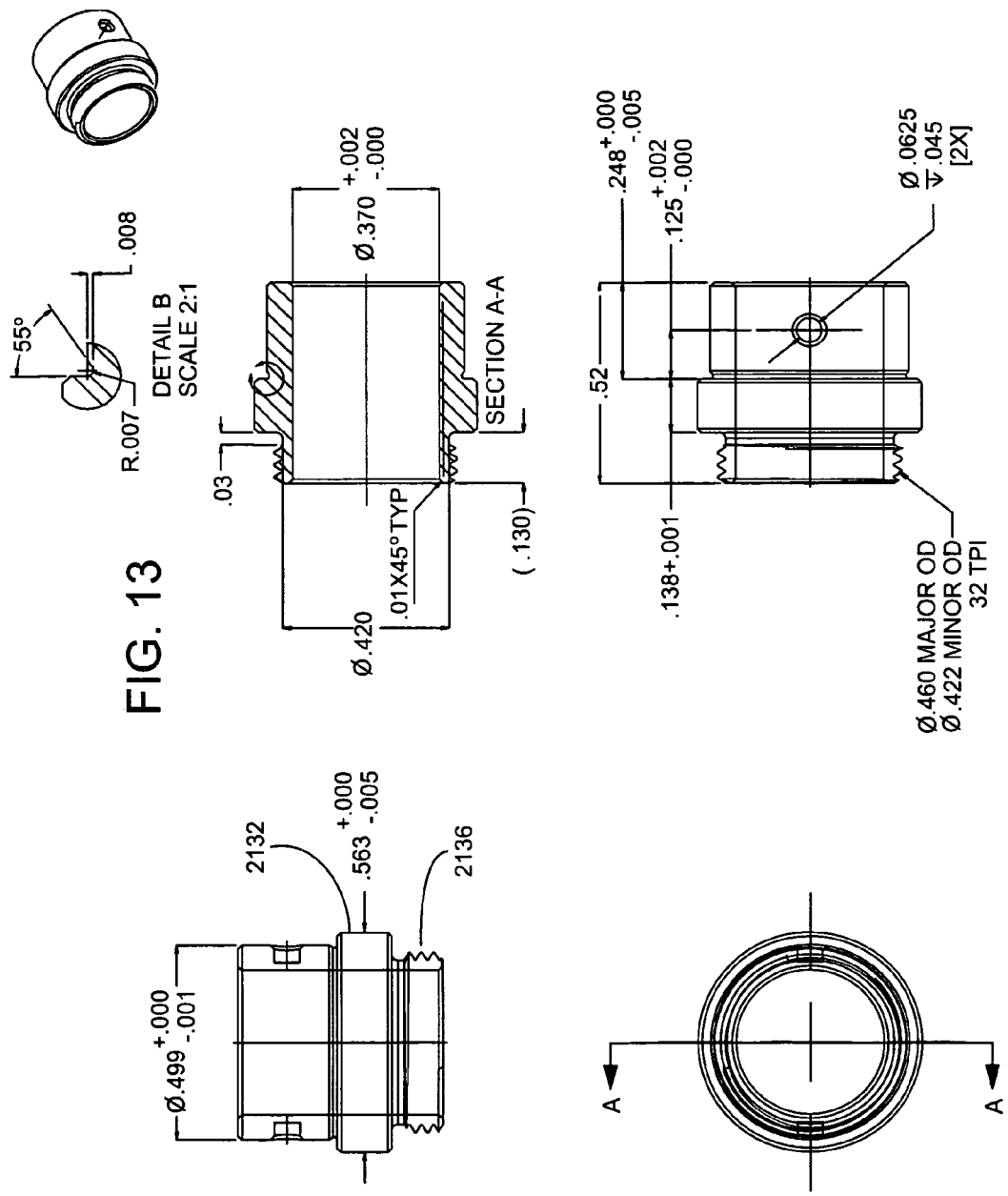
Figure 14:
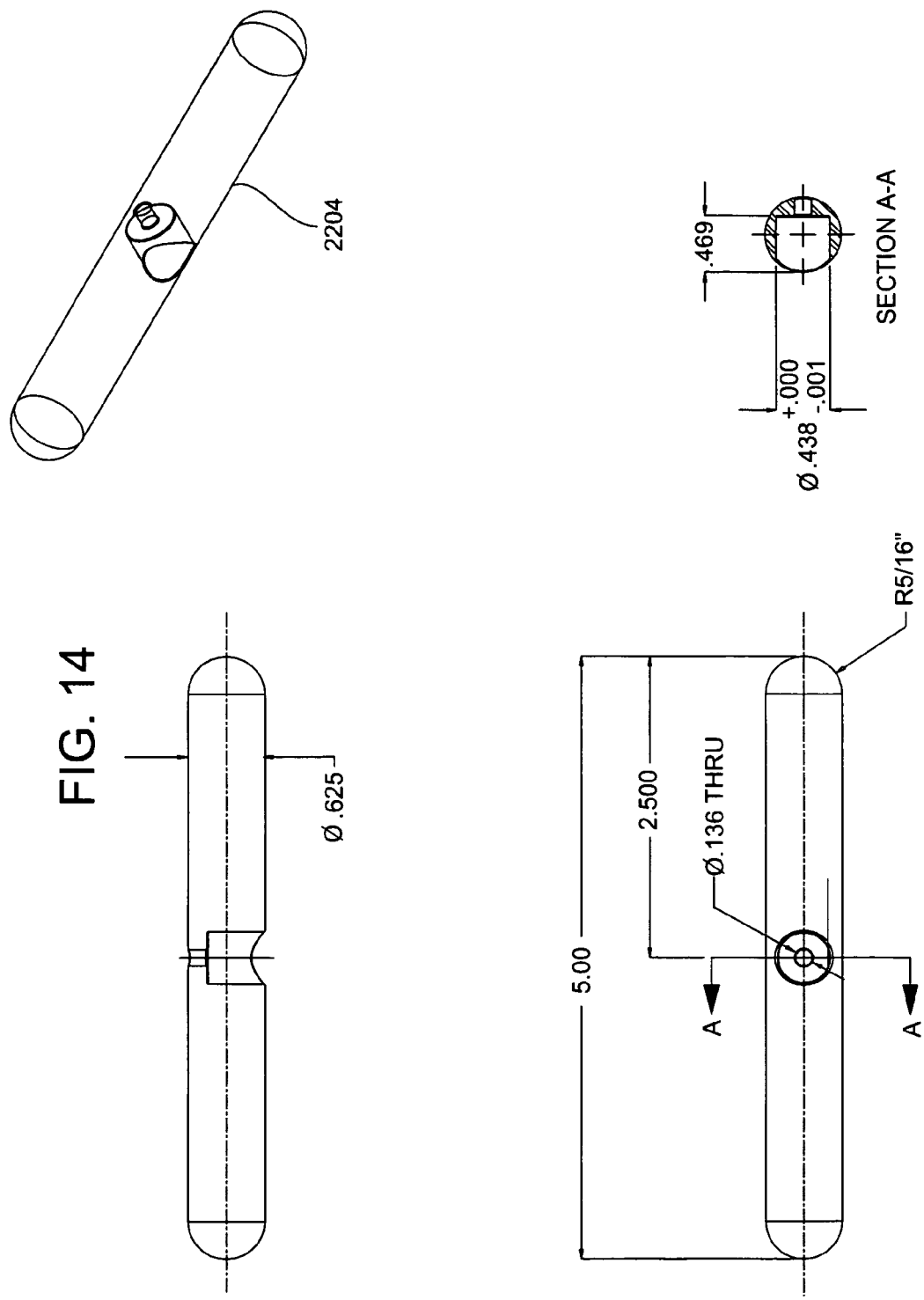
Figure 15:
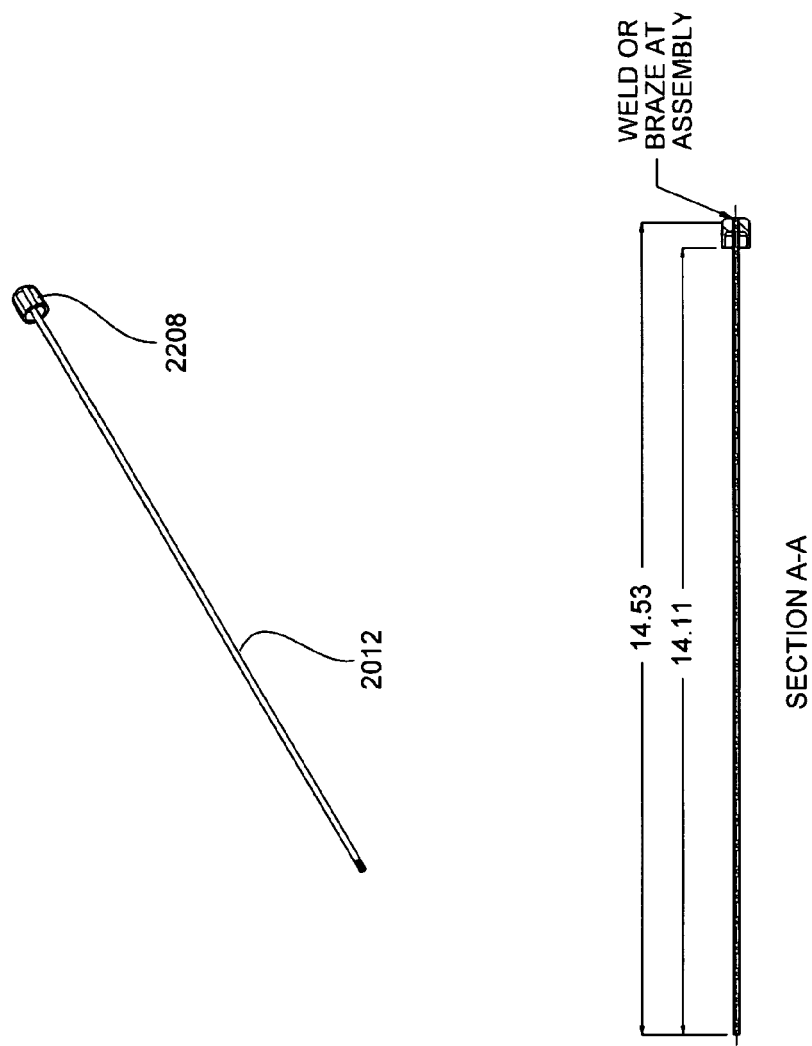
Figure 16:
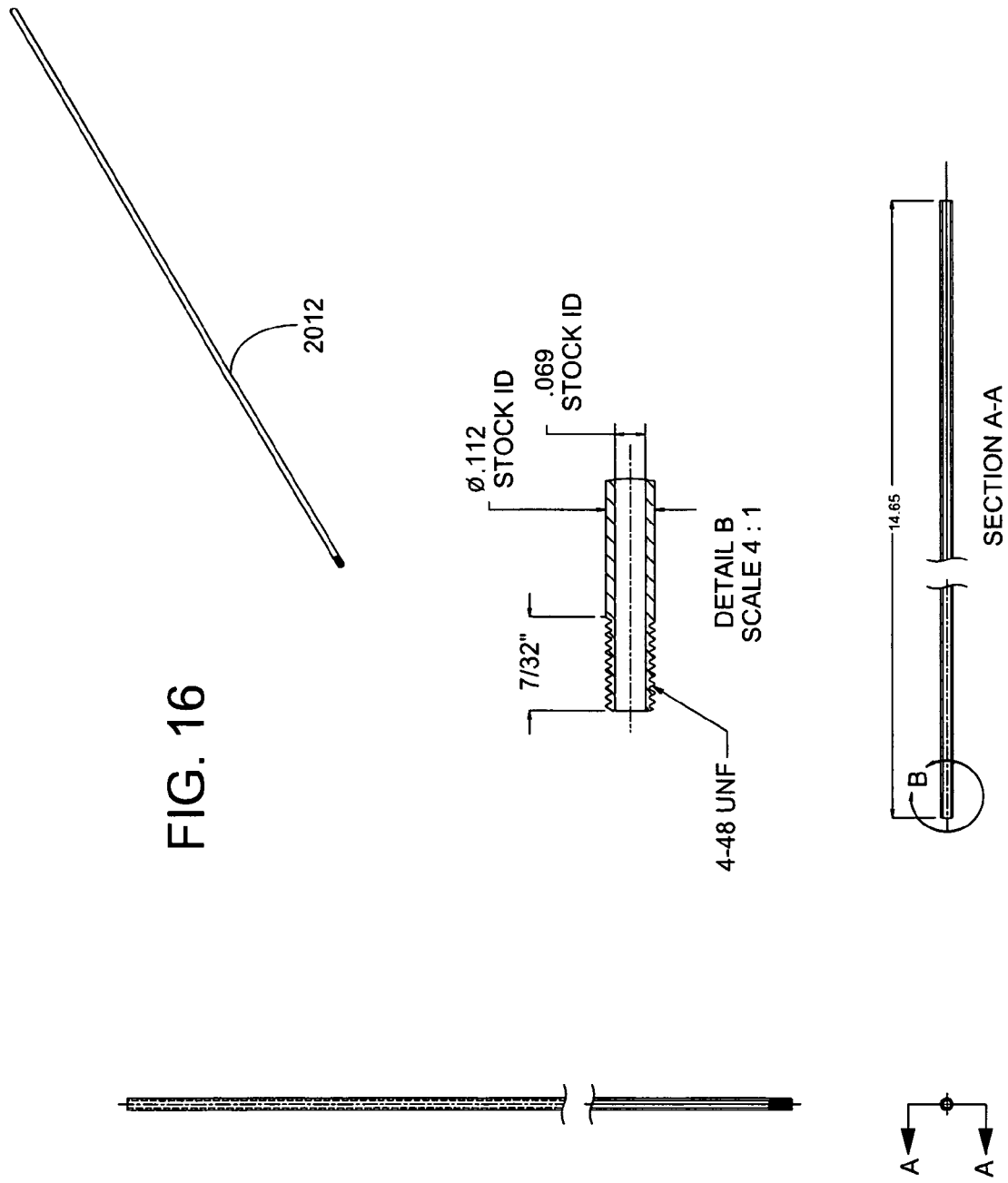

As shown in FIG. 10, polygonal torque driver 2104 has a hollow cavity 2224 running along its longitudinal axis which is used by the retention rod 2012. This same cavity 2224 could be connected through apertures (not shown) to deliver flowable material between the distal component 2108 and the proximal component 2112 into the intervertebral disc space. A variety of biomaterials can be delivered. Examples include curable elastomers, hydrogels, and blends of elastomers and hydrogels. While the cavity 364 in the distal end of the distal component is open to allow a loaded driver assembly to be deployed over a guide wire, this should not present a problem while injecting material. The opening to the cavity 364 will often be contained within the distal vertebral body (See FIG. 3). However, the retention rod or some other delivery device could be used to deliver a plug to this cavity 364 after it has served its purpose with respect to the guide wire.

EXAMPLE C

FIG. 17 shows an alternative torque driver 2230 with apertures 2234. A dual hex head driver 2230 of this type is adapted for use when the cross section of the distal component is reduced relative to the cross section of the proximal component such as illustrated in FIG. 5B, typically when dissimilar thread pitch is being used to provide distraction. After distraction, a driver assembly using the dual hex head driver 2230 can be left in place, that is with the driver maintaining the relative position of the two components as one component is held by engagement with the distal portion of the dual hex head driver 2230 by the retention rod and the other component is held in engagement with a more proximal portion of the dual hex head driver by the coupling. FIG. 18A provides an exploded diagram showing the use of an O-Ring to help limit the undesired flow of injected material into the driver assembly. FIGS. 18B and 18C illustrate other details of the interaction between the dual hex head driver and other system components.

A dual hex head driver is a descriptive name for the driver shown in FIGS. 17 and 18 but one of skill in the art will recognize that other polygonal shapes are viable.

The dual hex head driver and the polygonal torque driver described in connection with Example A can be manufactured in a variety of lengths so that the drivers can maintain the distal and proximal components at relative axial distances that are appropriate for both timed delivery of the proximal component (if timed delivery is used to avoid cross threading) and to adjust to the variations in anatomy between patients and the desired level of distraction.

EXAMPLE D

Figure 19:
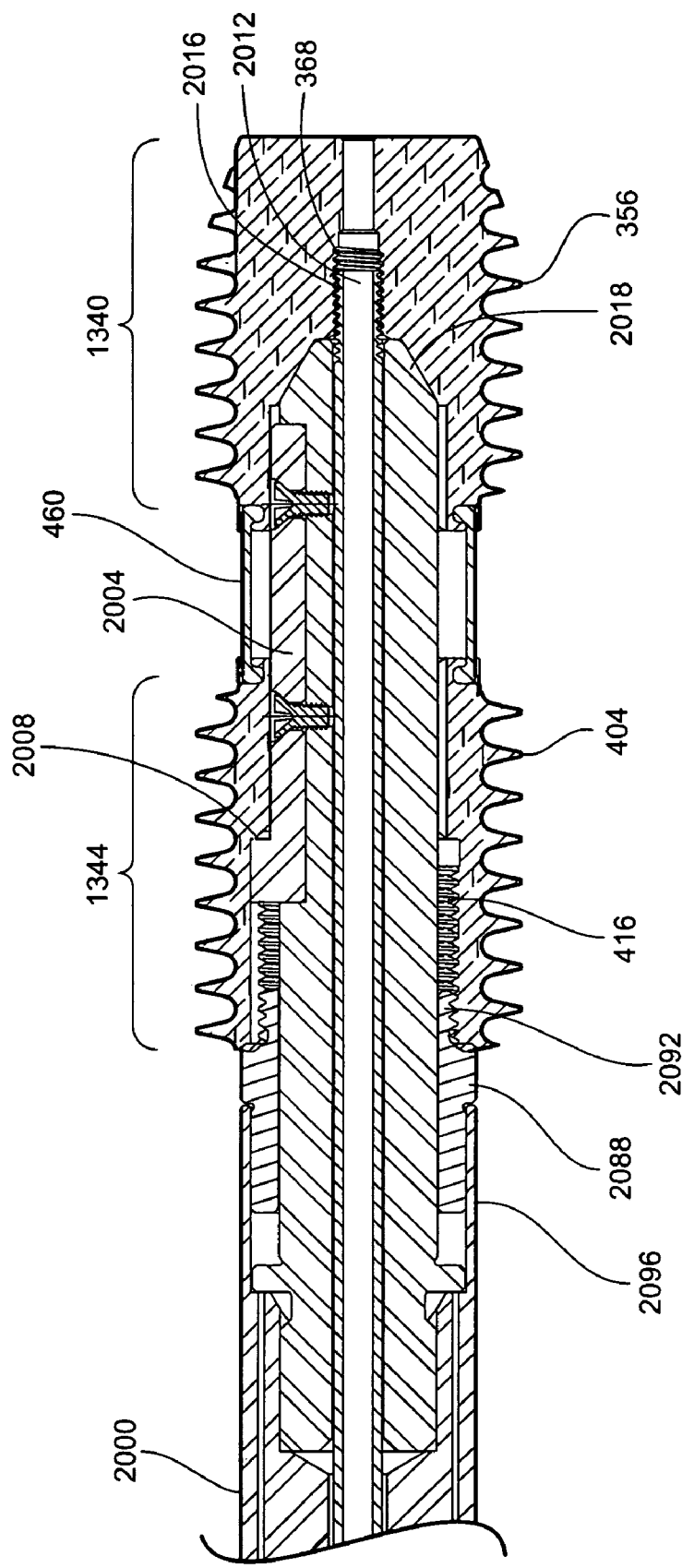
FIG. 19 shows the cross section of a keyed driver assembly for delivery of two implanted components.

FIG. 19 shows a distal bone anchor 1340 and a proximal bone anchor 1344 with a membrane 460 connected to the distal bone anchor 1340 and the proximal bone anchor 1344. In this example, the thread pitch of the external threads 356 on the distal bone anchor are the same as the thread pitch on the set of external threads 404 on the proximal bone anchor. The keyed driver assembly 2000 has a key 2004 with a shoulder 2008. The key 2004 slides in the slots in the proximal bone anchor and the distal bone anchor (previously discussed). The keyed driver assembly 2000 thus prevents the proximal bone anchor 1344 from rotating relative to the distal bone anchor 1340. Keying along with precise control of the distance between the bone anchors allows the leading edge of the external thread on the proximal bone anchor to enter into the proximal vertebral body into the beginning of the thread path left by the distal bone anchor as it was rotated up through the proximal vertebral body while moving towards the distal vertebral body.

A retention rod 2012 with external thread 2016 engages with the internal threaded section 368 of the distal bone anchor 1340. The retention rod 2012 can be rotated relative to the driver tip 2018 so that the distal bone anchor 1340 is pulled to contact the driver tip 2018.

Likewise a proximal anchor retention coupler 2088 with external threads 2092 can rotate relative to the driver tip 2018 as the proximal anchor retention coupler 2088 is attached to an external sheath 2096. Rotation of the proximal anchor retention coupler 2088 causes engagement between the external threads 2092 and the internal threads 416 of the proximal anchor 1344 to draw the proximal anchor 1344 down onto the shoulder 2008. With both anchors retained in contact with components of the keyed driver assembly 2000 the position of the distal bone anchor 1340 relative to the proximal bone anchor 1344 can be set based on the distances between the shoulder 2008 and the driver tip 2018. Control over the distances between the two separate bone anchors allows the two bone anchors with the same major diameter to be inserted without cross threading of the proximal vertebral body.

EXAMPLE E

Figure 20:
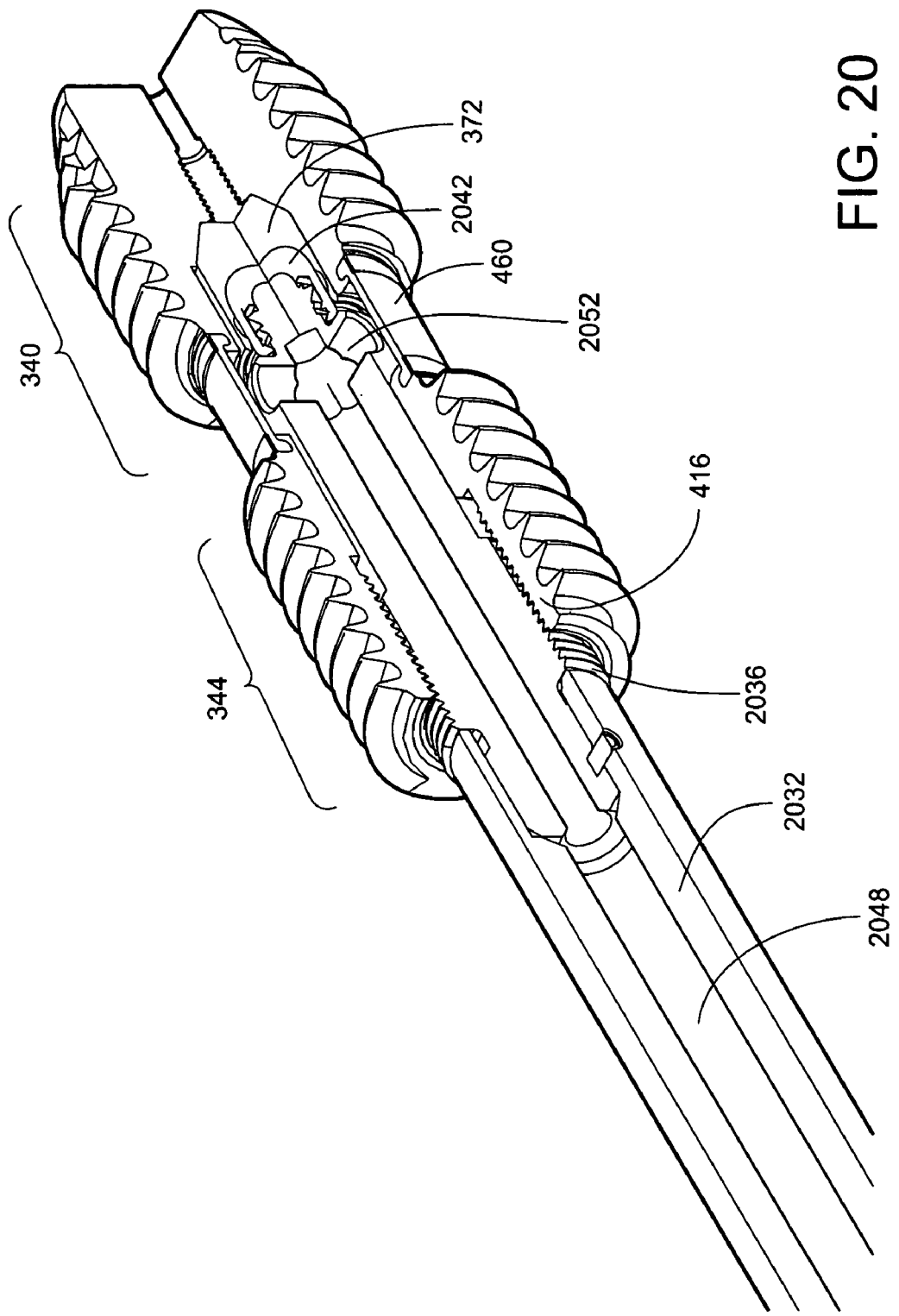
FIG. 20 shows a perspective view with a quarter round removed from a distractor/injector tool.

FIG. 20 show the use of a distractor/injector that is used after the components have been implanted in the proximal and distal vertebral bodies and the implant driver removed. This type of distractor/injector is useful when additional components need to be inserted into the distal bone anchor 340 before the injection of prosthetic nucleus material. In the instance shown in FIG. 20, a distal pivot cup 372 that will serve as the bearing surface for a pivot (not shown here but see FIG. 3) has been inserted in an implanted distal bone anchor. The bone anchors could be implanted with an driver assembly of the type discussed in Example A and FIG. 6, or if the distal and proximal components had a slot for keyed delivery, a driver assembly of the type discussed in connection FIG. 19 could be used.

FIG. 20 shows a distraction and insertion tool 2032 used to distract the motion segment then deploy prosthetic nucleus material in to the membrane 460 to distend the membrane 460 to a conforming fit within the space of the intervertebral disc space. The insertion tool 2032 has a set of external threads 2036 which engage with a set of internal threads 416 in the proximal bone anchor 344. The distal end of the insertion tool 2032 is an atraumatic tip 2042 designed to contact without damaging the bearing surface in the distal pivot cup 372. Axially advancing the distraction and insertion tool 2032 pushes the atraumatic tip 2042 on the distal pivot cup 372 to move the vertebral body engaged with the distal bone anchor 340 relative to the vertebral body engaged with the proximal bone anchor 344. After achieving the desired amount of distraction an internal channel 2048 is used to provide prosthetic nucleus material to be delivered through a set of fenestrations 2052 to fill and expand the membrane 460. The prosthetic nucleus material is inserted until there is a conforming fit between the membrane 460 and the endplates of the two vertebral bodies and the wall of the annulus fibrosus.

After the prosthetic nucleus material is allowed to cure, the insertion tool 2032 can be removed leaving behind a void in the prosthetic nucleus material where the insertion tool was during the formation of the prosthetic nucleus. (see element 348 on FIG. 3).

Figure 21:
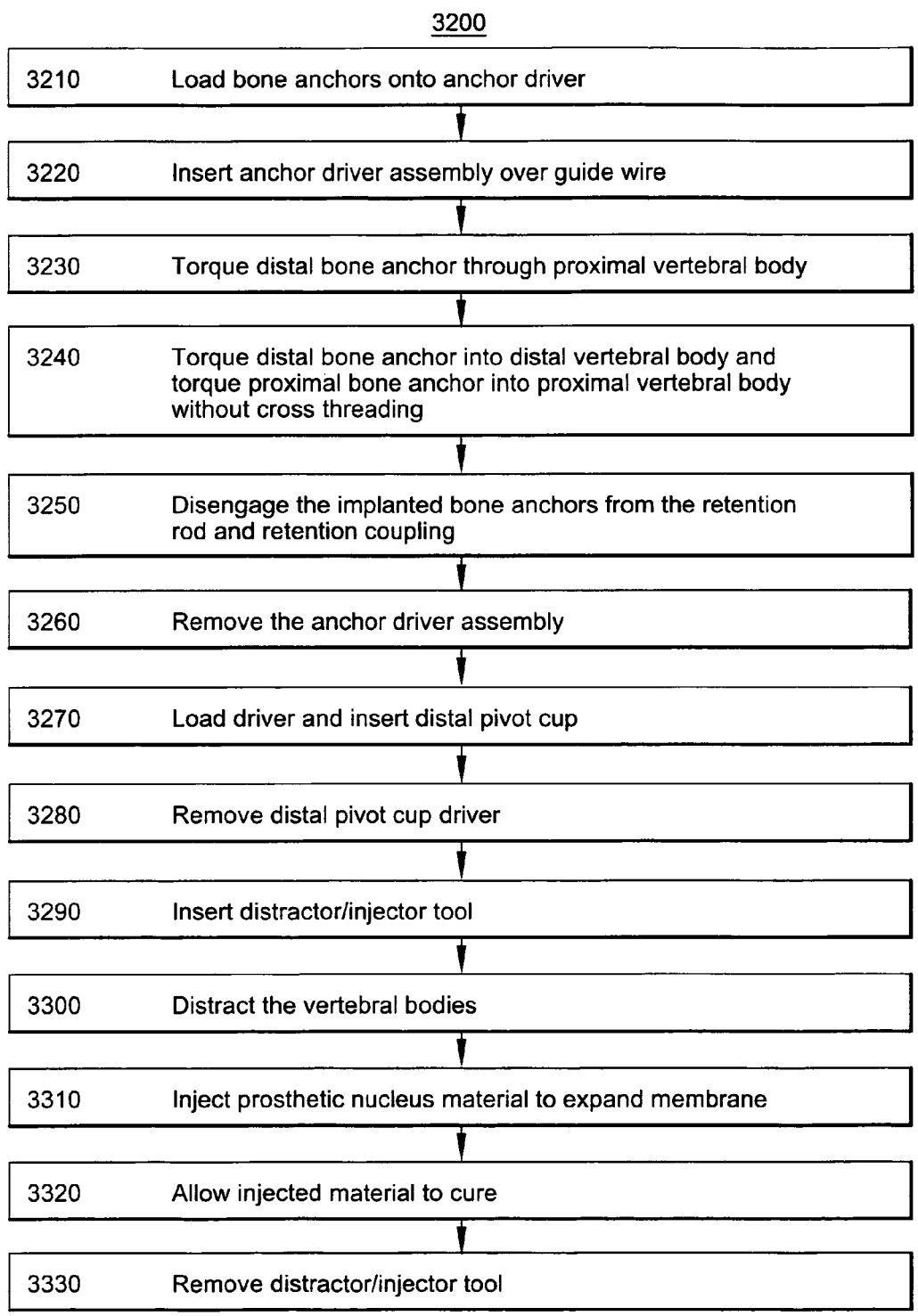
FIG. 21 is a flow chart describing a particular method for deployment of a motion preservation assembly.

The process 3200 for using a driver to first implant the distal and proximal devices, then insert one or more components before inserting a different tool to distract and then inject prosthetic nucleus material is summarized in FIG. 21.

Step 3210 Load the device driver assembly with both the distal and proximal components. These two anchors, connected by a flexible membrane, are placed on the anchor driver assembly. The driver assembly uses an elongated torque driver, in this case a hexagonal shaped toque driver with an elongated section with a constant cross sectional (taken perpendicular to the longitudinal axis).

The step of loading the driver assembly includes seating the distal component onto the distal end of the driver wherein it is retained on the tip during insertion and axial, distal advancement by means of a threaded retention rod, and seating the proximal bone anchor on a shoulder within the dual anchor driver assembly through use of a proximal anchor retention coupler. Seating the two bone anchors on the driver assembly maintains a predetermined spatial separation between the distal component and proximal component and stretches the flexible membrane located there between so that the membrane slightly "necks in" and is less likely to be damaged while passing through the proximal vertebral body.

Step 3220 Insert the anchor driver assembly over a guide wire and advance the anchor driver assembly through the previously prepared axial channel that includes a bore through the proximal vertebral body and a bore in the distal vertebral body. The bore hole in the proximal vertebral body is about the size of the minor diameter of the external threads on both bone anchors.

Step 3230 Torque is applied using the anchor driver assembly to rotate and axially advance the distal bone anchor through the proximal vertebral body thereby creating a helical thread path through the first vertebral body.

Step 3240 Continued application of torque axially advances the bone anchors, which are held on the anchor driver assembly at a spatially maintained distance, to anchor the distal component into the distal vertebral body and anchor the proximal component into the proximal vertebral body without cross threading or rethreading in the proximal vertebral body.

Step 3250 Once the bone anchors are positioned into the respective vertebral bodies, release the distal bone anchor from the threaded engagement with the retention rod and release the proximal bone anchor from the proximal anchor retention coupler as the retention rod and the proximal anchor retention coupler can be rotated relative to the elongated hexagonal hex driver.

Step 3260 Remove the anchor driver assembly.

Step 3270 Insert the distal pivot cup by engaging the distal pivot cup with driver (not shown here) that employs a detent mechanism to engage the distal pivot cup. (Those with an interest in this particular driver can find it described in detail in co-pending application Ser. No. 11/256,810 which has been incorporated by reference.

Step 3280 Disengage the distal pivot cup driver from the distal pivot cup and remove the distal pivot cup driver.

Step 3290 Insert distractor/injector tool into the implanted bone anchors so that atraumatic tip of the distractor/injector tool contacts the distal pivot cup bearing surface. As it is undesirable to scratch or otherwise mar the bearing surface. The material selected for the atraumatic tip may be advantageously selected to be less hard than the bearing surface and smooth so it is not apt to scratch the bearing surface.

Step 3300 Move the distal vertebral body relative to the proximal vertebral body by axially advancing the distractor/injector tool relative to the proximal bone anchor through threaded engagement within the proximal bone anchor to push via an atraumatic tip on the distal pivot cup.

Step 3310 Inject prosthetic nucleus material through the interior of the distractor/injector and out apertures in fluid communication between the interior of the distractor/injector and the flexible membrane to expand and fill the flexible membrane sufficiently to form the prosthetic nucleus component of this prosthetic disc device, the prosthetic nucleus component being in conformal contact with the surfaces of the intervertebral disc space.

Step 3320 Allow the injected material to cure.

Step 3330 Remove the distractor/injector tool. This will leave a void in the cured injected material where the tool occupied volume in the intervertebral disc space during injection and curing. The cured prosthetic nucleus material should substantially retain the distraction imposed between the vertebral bodies. Subsequent processing steps during assembly of the spinal implant assembly could include a minor secondary distraction. Alternatively, the original distraction could be increased a small amount to compensate for any movement of cured injected material towards the void left by the removal of the distractor/injector.

There would be subsequent steps to complete the assembly of the particular spinal implant assembly and to close the surgical site but those steps are beyond the focus of the present invention.

Preferred materials for the various components shown in the drivers described above include components that are formed, i.e., machined, from among high strength (e.g., high tensile strength, high fatigue strength), wear and abrasion resistant metal alloys (e.g., MP35N; Elgiloy™, a super alloy of cobalt chrome; Co—Cr alloy such as Stellite™; Ti6Al4V alloy, and nitride coated Ti alloys) according to the biomechanical properties being selected by design (e.g., ability of driver to withstand torque while rotating to axially advance dual anchor implants through and into vertebral bone).

Injection Details

Whether done via a driver/injector or a distractor/injector tool, the membrane is expanded by means of high pressure injection, with a syringe, of prosthetic nucleus material (PNM) (e.g., saline, viscoelastic gel or an elastomeric solid or blends or combinations thereof), that is engaged by means of an integral Luer lock fitting that is configured to engage the handle at the proximal end of the MPA distractor/injector. A delivery tube or catheter, wherein the distal end of the tube is configured to engage the fitting in proximal end of the tool, and the proximal end of the tube engages a syringe attached thereon. The expandable membrane is enlarged or filled by means of apertures or fenestrations, e.g., through the slits or "cuts" in the cannulated rod comprising the in the torque driver (such as the dual hex head driver discussed above) or the distractor/injector tool, which enable fluid communication between the exterior and interior of the driver of the and through which prosthetic nucleus material is injected into the disc space, either directly, or via an intermediate (from about 6-12 mm of the overall deployed implant length) expandable membrane configured to be adhesively affixed and engaged by laser welding of a retainer ring, to or into the distal end of the proximal threaded anchor component and the proximal end of the distal threaded anchor component, respectively. In this manner, the expandable membrane inflates and extends into the intervertebral disc space previously distracted by means of the driver/injector or distractor/injector of the present invention, until when filled, it conformably contacts the surfaces within the intervertebral disc space. The ultimate expansion of the membrane is limited by contact with the end plates and the annulus, preventing rupture of the membrane due to over inflation. When filled and expanded in this manner with a suitable PNM, e.g., a hydrogel selected at least in part based on viscoelastic properties, the MPA is enabled to biomechanically perform the intended function of the motion restoration segment, e.g., the membrane, when filled with PNM, transfers hydrostatic pressure within the nuclear space into tensile "hoop stresses" in the annulus.

In one aspect of the invention, driver/injectors or distractor/injectors are configured to accommodate injection means with sufficient pressure/forces of substantially about 300 psi to deliver the PNM (or therapeutic, e.g., drug materials delivery) without accompanying shear forces that would fragment; denaturate; modify viscoelastic properties, e.g., rheology and/or compressibility; or otherwise render the therapeutic materials or PNM ineffective for their intended functionality (e.g., biomechanical motion segment mobility restoration/preservation in the case of PND with PNM). In a preferred embodiment, driver/injectors or distractor/injectors comprise at least one O-ring to enable injection of fluid(s) under pressure.

One of skill in the art will recognize that the alternative embodiments set forth above are not universally mutually exclusive and that in some cases alternative embodiments can be created that employ two or more of the variations described above. Likewise, the present invention is not limited to the specific examples or particular embodiments provided to promote understanding of the present invention. Moreover, the scope of the present invention covers the range of variations, modifications, and substitutes for the components described herein as would be known to those of skill in the art.

The legal limitations of the scope of the claimed invention are set forth in the claims that follow and extend to cover their legal equivalents. Those unfamiliar with the legal tests for equivalency should consult a person registered to practice before the United States Patent and Trademark Office.

What is claimed is:

1. An apparatus with a distal end and a proximal end to deliver a spinal implant assembly to a motion segment, the implant assembly comprising a distal component and a proximal component;

the apparatus configured to receive the proximal component and to hold the proximal component on the apparatus by pulling the proximal component towards the proximal end of the apparatus, the apparatus configured to receive the distal component and to hold the distal component on the apparatus by pulling the distal component towards the proximal end of the apparatus, such that the apparatus establishes and maintains a specific relative axial spacing between the distal component and the proximal component;

the apparatus configured to simultaneously rotatably drive the distal component and the proximal component into the motion segment and to maintain the specific relative axial spacing between the distal component and the proximal component, and the apparatus having a set of interchangeable elongated polygonal driver components of different lengths can be used to select a particular specific relative axial spacing to be maintained between the distal component and the proximal component.

2. The apparatus of claim 1 further comprising a threaded retainer rod to engage the distal component by rotating relative to the driver component and a threaded coupler to engage the proximal component while rotating relative to the driver component.

3. The apparatus of claim 1 wherein the apparatus is adapted for use in an axial channel in the spine accessed through a trans-sacral approach.

4. The apparatus of claim 1 wherein at least a portion of the elongated polygonal driver is hexagonal shaped.

5. The apparatus of claim 1 wherein the apparatus has a key which engages with corresponding slots on the distal component and the proximal component.

6. The apparatus of claim 1 wherein the apparatus is adapted to rotatably drive the distal component through a proximal vertebral body and then subsequently drive the proximal component into the proximal vertebral body through timed delivery of a set of external threads on the proximal component to a helical thread path cut in the proximal vertebral body by the distal component.

7. The apparatus of claim 6 wherein the adaptation of the apparatus comprises selecting the relative axial spacing between the distal component and the proximal component based in part on the thread pitch used in a set of external threads on the distal component and used in the set of external threads on the proximal component.

8. The apparatus of claim 7 wherein the apparatus is adapted to allow delivery of a flowable biomaterial to an intervertebral disc space located between the distal component and the proximal component.

9. The apparatus of claim 8 wherein the flowable biomaterial is an in situ curing elastomer.

10. The apparatus of claim 9 wherein the elastomer is comprised of silicone.

11. The apparatus of claim 7 wherein the apparatus has a shoulder section for engagement with the proximal component.

12. The apparatus of claim 7 wherein the adaptation of the apparatus comprises selecting the relative axial spacing between the distal component and the proximal component based in part on the anatomy of the motion segment for the intended recipient of the spinal implant assembly.

13. The apparatus of claim 8 wherein the flowable biomaterial is a hydrogel.

14. The apparatus of claim 8 wherein the flowable biomaterial is a blend of hydrogel and elastomer.

15. The apparatus of claim 1 further adapted for deployment over a guide wire.

16. The apparatus of claim 1 wherein the apparatus has a dual hex head driver.

17. The apparatus of claim 1 further adapted to simultaneously drive a proximal component with a first cross section and a distal component with a second smaller cross section through use of a dual headed polygonal torque driver.

18. An apparatus with a distal end and a proximal end to deliver a spinal implant assembly to a motion segment, the implant assembly comprising a distal component and a proximal component;
the apparatus configured to receive the proximal component and to hold the proximal component on the apparatus by pulling the proximal component towards the proximal end of the apparatus through use of a threaded coupler adapted to engage the proximal component while rotating relative to the driver component,
the apparatus configured to receive the distal component and to hold the distal component on the apparatus by pulling the distal component towards the proximal end of the apparatus, through use of a threaded retainer rod adapted to engage the distal component by rotating relative to the distal component such that the apparatus establishes and maintains a specific relative axial spacing between the distal component and the proximal component;
the apparatus configured to simultaneously rotatably drive the distal component and the proximal component into the motion segment and to maintain the specific relative axial spacing between the distal component and the proximal component.

19. The apparatus of claim 18 wherein the apparatus is adapted for use in an axial channel in the spine accessed through a trans-sacral approach.

20. The apparatus of claim 18 wherein the apparatus has an elongated polygonal driver component.

21. The apparatus of claim 20 wherein at least a portion of the elongated polygonal driver is hexagonal shaped.

22. The apparatus of claim 18 wherein the apparatus is adapted to rotatably drive the distal component through a proximal vertebral body and then subsequently drive the proximal component into the proximal vertebral body through timed delivery of a set of external threads on the proximal component to a helical thread path cut in the proximal vertebral body by the distal component.

23. The apparatus of claim 22 wherein the adaptation of the apparatus comprises selecting the relative axial spacing between the distal component and the proximal component based in part on the thread pitch used in a set of external threads on the distal component and used in the set of external threads on the proximal component.

24. The apparatus of claim 23 wherein the apparatus is adapted to allow delivery of a flowable biomaterial to an intervertebral disc space located between the distal component and the proximal component.

25. The apparatus of claim 24 wherein the flowable biomaterial is an in situ curing elastomer.

26. The apparatus of claim 25 wherein the elastomer is comprised of silicone.

27. The apparatus of claim 22 wherein the adaptation of the apparatus comprises selecting the relative axial spacing between the distal component and the proximal component based in part on the anatomy of the motion segment for the intended recipient of the spinal implant assembly.

28. The apparatus of claim 23 wherein the apparatus has a shoulder section for engagement with the proximal component.

29. The apparatus of claim 24 wherein the flowable biomaterial is a hydrogel.

30. The apparatus of claim 24 wherein the flowable biomaterial is a blend of hydrogel and elastomer.

31. The apparatus of claim 18 wherein the apparatus has a key which engages with corresponding slots on the distal component and the proximal component.

32. The apparatus of claim 18 further adapted for deployment over a guide wire.

33. The apparatus of claim 18 wherein the apparatus has a dual hex head driver.

34. The apparatus of claim 18 further adapted to simultaneously drive a proximal component with a first cross section and a distal component with a second smaller cross section through use of a dual headed polygonal torque driver.

35. The apparatus of claim 18 wherein a set of interchangeable elongated polygonal driver components of different lengths can be used to select a particular specific relative axial spacing to be maintained between the distal component and the proximal component.

\* \* \* \* \*